(12) United States Patent
McMorrow et al.

(10) Patent No.: US 8,221,321 B2
(45) Date of Patent: Jul. 17, 2012

(54) SYSTEMS AND METHODS FOR QUANTIFICATION AND CLASSIFICATION OF FLUIDS IN HUMAN CAVITIES IN ULTRASOUND IMAGES

(75) Inventors: Gerald McMorrow, Kirkland, WA (US); Vikram Chalana, Mill Creek, WA (US); Jongtae Yuk, Redmond, WA (US); Henri Baartmans, Ijsselstein (NL); Nicolaas Bom, Berkenwoude (NL); Charles Theodoor Lancee, Hoogersmilde (NL); Egon J. W. Merks, Delft (NL)

(73) Assignee: Verathon Inc., Bothell, WA (US)

(*) Notice: Subject to any disclaimer, the term of this patent is extended or adjusted under 35 U.S.C. 154(b) by 698 days.

(21) Appl. No.: 11/213,284

(22) Filed: Aug. 26, 2005

(65) Prior Publication Data

US 2006/0079775 A1 Apr. 13, 2006

Related U.S. Application Data

(63) Continuation-in-part of application No. 10/523,681, filed as application No. PCT/EP03/07807 on Jul. 1, 2003, application No. 11/213,284, which is a continuation-in-part of application No. 11/119,355, filed on Apr. 29, 2005, now Pat. No. 7,520,857, which is a continuation-in-part of application No. 10/701,955, filed on Nov. 5, 2003, now Pat. No.

(Continued)

(60) Provisional application No. 60/566,127, filed on Apr. 30, 2004, provisional application No. 60/545,576, filed on Feb. 17, 2004, provisional application No. 60/566,818, filed on Apr. 30, 2004, provisional application No. 60/633,485, filed on Dec. 6, 2004, provisional application No. 60/608,426, filed on Sep. 9, 2004, provisional application No. 60/605,391, filed on Aug. 27, 2004, provisional application No. 60/423,881, filed on Nov. 5, 2002, provisional application No. 60/400,624, filed on Aug. 2, 2002, provisional application No. 60/470,525, filed on May 12, 2003.

(30) Foreign Application Priority Data

Aug. 9, 2002 (GB) .................................. 0218547.8

(51) Int. Cl.
*A61B 8/00* (2006.01)
(52) U.S. Cl. ........ 600/437; 600/439; 600/472; 600/441; 600/447; 382/128
(58) Field of Classification Search .......... 600/437–472; 382/128, 168, 181–231
See application file for complete search history.

(56) References Cited

U.S. PATENT DOCUMENTS 3,613,069 A 10/1971 Cary, Jr.
(Continued)

FOREIGN PATENT DOCUMENTS

EP 0 271 214 6/1988
(Continued)

OTHER PUBLICATIONS

Baker, A., et al.: "Distortion and High-Frequency Generation Due to Nonlinear Propagation of Short Ultrasonic Pulses from a Plane Circular Piston", Journal of Acoustical Society of America, vol. 92, No. 3, pp. 1699-1705, Sep. 1992.

(Continued)

*Primary Examiner* — Brian Casler
*Assistant Examiner* — Joel Lamprecht
(74) *Attorney, Agent, or Firm* — Scott Born; Foster Pepper PLLC

(57) ABSTRACT

Ultrasound imaging systems and methods are disclosed. In one embodiment, an ultrasonography method includes creating a database that is representative of a tissue, a fluid, or a cavity of a body, and transmitting ultrasound pulses into a region-of-interest in a patient. Echoes are received from the region of interest, and based upon the received echoes, compiling an ultrasonic pattern of the region-of-interest is compiled. The pattern is processed by comparing the region-of-interest patterns to the pattern information stored in the database. A composition within the region-of-interest of the patient is then determined.

23 Claims, 17 Drawing Sheets

Related U.S. Application Data 7,087,022, which is a continuation-in-part of application No. 10/443,126, filed on May 20, 2003, now Pat. No. 7,041,059, said application No. 11/213,284 is a continuation-in-part of application No. 11/061,867, filed on Feb. 17, 2005, now Pat. No. 7,611,466, and a continuation-in-part of application No. 10/704,996, filed on Nov. 10, 2003, now abandoned, which is a continuation-in-part of application No. 10/701,955, filed on Nov. 5, 2003, now Pat. No. 7,087,022, said application No. 11/213,284 is a continuation-in-part of application No. 10/165,556, filed on Jun. 7, 2002, now Pat. No. 6,676,605, and a continuation-in-part of application No. PCT/US03/24368, filed on Aug. 1, 2003, and a continuation-in-part of application No. PCT/US03/14785, filed on May 9, 2003, which is a continuation of application No. 10/165,556, filed on Jun. 7, 2002, now Pat. No. 6,676,605, said application No. 11/213,284 is a continuation-in-part of application No. 10/633,186, filed on Jul. 31, 2003, now Pat. No. 7,004,904.

(56) References Cited

U.S. PATENT DOCUMENTS

| | | | | |
|---|---|---|---|---|
| 4,431,007 | A | 2/1984 | Amazeen et al. | 128/660 |
| 4,556,066 | A | 12/1985 | Semrow | 128/660 |
| 4,757,821 | A | 7/1988 | Snyder | 128/660 |
| 4,771,205 | A | 9/1988 | Mequio | 310/334 |
| 4,821,210 | A | 4/1989 | Rumbaugh | 364/518 |
| 4,844,080 | A | 7/1989 | Frass et al. | 128/660.01 |
| 4,926,871 | A | 5/1990 | Ganguly et al. | 128/660.07 |
| 5,058,591 | A | 10/1991 | Companion et al. | 128/661.03 |
| 5,060,515 | A | 10/1991 | Kanda et al. | 73/602 |
| 5,078,149 | A | 1/1992 | Katsumata et al. | 128/662.03 |
| 5,125,410 | A | 6/1992 | Misono et al. | 128/662.06 |
| 5,148,809 | A | 9/1992 | Biegeleisen-Knight et al. | 128/660.07 |
| 5,151,856 | A | 9/1992 | Halmann et al. | 364/413.03 |
| 5,159,931 | A | 11/1992 | Pini | 128/660.07 |
| 5,197,019 | A | 3/1993 | Delon-Martin et al. | 364/563 |
| 5,235,985 | A | 8/1993 | McMorrow et al. | |
| 5,265,614 | A | 11/1993 | Hayakawa et al. | 128/602.03 |
| 5,299,577 | A | 4/1994 | Brown et al. | 128/660.07 |
| 5,381,794 | A | 1/1995 | Tei et al. | 128/662.03 |
| 5,432,310 | A | 7/1995 | Stoeger | 200/82 R |
| 5,435,310 | A | 7/1995 | Sheehan et al. | 128/653.1 |
| 5,465,721 | A | 11/1995 | Kishimoto et al. | 128/660.07 |
| 5,473,555 | A | 12/1995 | Potter | 364/724.1 |
| 5,487,388 | A | 1/1996 | Rello et al. | 128/660.09 |
| 5,503,152 | A | 4/1996 | Oakley et al. | 128/661.01 |
| 5,503,153 | A | 4/1996 | Liu et al. | 128/661.08 |
| 5,526,816 | A | 6/1996 | Arditi | 128/662.02 |
| 5,553,618 | A | 9/1996 | Suzuki et al. | 128/653.1 |
| 5,575,286 | A | 11/1996 | Weng et al. | 128/653.1 |
| 5,575,291 | A | 11/1996 | Hayakawa et al. | 128/662.03 |
| 5,577,506 | A | 11/1996 | Dias | 128/662.03 |
| 5,588,435 | A | 12/1996 | Weng et al. | |
| 5,601,084 | A | 2/1997 | Sheehan et al. | 128/661.04 |
| 5,605,155 | A | 2/1997 | Chalana et al. | 128/660.07 |
| 5,615,680 | A | 4/1997 | Sano | 128/661.09 |
| 5,644,513 | A | 7/1997 | Rudin et al. | 364/572 |
| 5,645,077 | A | 7/1997 | Foxlin | 128/774 |
| 5,697,525 | A | 12/1997 | O'Reilly et al. | 222/105 |
| 5,698,549 | A | 12/1997 | Steers et al. | 514/211 |
| 5,724,101 | A | 3/1998 | Haskin | 348/441 |
| 5,735,282 | A | 4/1998 | Hossack | 128/662.03 |
| 5,738,097 | A | 4/1998 | Beach et al. | 128/661.09 |
| 5,776,063 | A | 7/1998 | Dittrich et al. | |
| 5,782,767 | A | 7/1998 | Pretlow, III | 600/443 |
| 5,806,521 | A | 9/1998 | Morimoto et al. | 128/661.01 |
| 5,841,889 | A | 11/1998 | Seyed-Bolorforosh | 382/128 |
| 5,846,202 | A | 12/1998 | Ramamurthy et al. | |
| 5,851,186 | A | 12/1998 | Wood et al. | 600/437 |
| 5,873,829 | A | 2/1999 | Kamiyama et al. | |
| 5,892,843 | A | 4/1999 | Zhou et al. | 382/176 |
| 5,898,793 | A | 4/1999 | Karron et al. | 382/131 |
| 5,903,664 | A | 5/1999 | Hartley et al. | 382/154 |
| 5,908,390 | A | 6/1999 | Matsushima | 600/447 |
| 5,913,823 | A | 6/1999 | Hedberg et al. | |
| 5,928,151 | A | 7/1999 | Hossack et al. | 600/443 |
| 5,945,770 | A | 8/1999 | Hanafy | 310/322 |
| 5,964,710 | A | 10/1999 | Ganguly et al. | 600/449 |
| 5,971,923 | A | 10/1999 | Finger | 600/437 |
| 5,972,023 | A | 10/1999 | Tanner et al. | 606/219 |
| 5,980,459 | A | 11/1999 | Chiao et al. | |
| 5,993,390 | A | 11/1999 | Savord et al. | 600/437 |
| 6,008,813 | A | 12/1999 | Lauer et al. | 345/424 |
| 6,030,344 | A | 2/2000 | Guracar et al. | |
| 6,042,545 | A | 3/2000 | Hossack et al. | 600/443 |
| 6,048,312 | A | 4/2000 | Ishrak et al. | 600/443 |
| 6,063,033 | A | 5/2000 | Haider et al. | 600/447 |
| 6,064,906 | A | 5/2000 | Langberg et al. | 600/518 |
| 6,071,242 | A | 6/2000 | Lin | 600/456 |
| 6,102,858 | A | 8/2000 | Hatfield et al. | 600/443 |
| 6,106,465 | A | 8/2000 | Napolitano et al. | |
| 6,110,111 | A | 8/2000 | Barnard | 600/438 |
| 6,117,080 | A | 9/2000 | Schwartz | 600/443 |
| 6,122,538 | A | 9/2000 | Sliwa, Jr. et al. | 600/407 |
| 6,123,669 | A | 9/2000 | Kanda | |
| 6,126,598 | A | 10/2000 | Entrekin et al. | 600/437 |
| 6,139,499 | A * | 10/2000 | Wilk | 600/443 |
| 6,142,942 | A | 11/2000 | Clark | 600/443 |
| 6,146,330 | A | 11/2000 | Tsujino et al. | |
| 6,148,095 | A | 11/2000 | Prause et al. | 382/131 |
| 6,151,404 | A | 11/2000 | Pieper | 382/128 |
| 6,159,150 | A | 12/2000 | Yale et al. | 600/437 |
| 6,171,248 | B1 | 1/2001 | Hossack et al. | 600/459 |
| 6,193,657 | B1 | 2/2001 | Drapkin | 600/437 |
| 6,200,266 | B1 | 3/2001 | Shokrollahi et al. | 600/438 |
| 6,210,327 | B1 | 4/2001 | Brackett et al. | 600/437 |
| 6,213,949 | B1 * | 4/2001 | Ganguly et al. | 600/449 |
| 6,213,951 | B1 | 4/2001 | Krishnan et al. | |
| 6,222,948 | B1 | 4/2001 | Hossack et al. | |
| 6,233,480 | B1 | 5/2001 | Hochman et al. | 600/476 |
| 6,238,344 | B1 | 5/2001 | Gamelsky et al. | 600/437 |
| 6,248,070 | B1 | 6/2001 | Kanda et al. | 600/443 |
| 6,254,539 | B1 | 7/2001 | Pang et al. | 600/443 |
| 6,264,609 | B1 | 7/2001 | Herrington et al. | 600/443 |
| 6,272,469 | B1 | 8/2001 | Koritzinsky et al. | 705/2 |
| 6,277,073 | B1 | 8/2001 | Bolorforosh et al. | |
| 6,286,513 | B1 | 9/2001 | Au et al. | 128/898 |
| 6,290,648 | B1 * | 9/2001 | Kamiyama | 600/443 |
| 6,302,845 | B2 | 10/2001 | Shi et al. | |
| 6,309,353 | B1 | 10/2001 | Cheng et al. | 600/437 |
| 6,325,758 | B1 | 12/2001 | Carol et al. | 600/439 |
| 6,338,716 | B1 | 1/2002 | Hossack et al. | 600/459 |
| 6,343,936 | B1 | 2/2002 | Kaufman et al. | 434/262 |
| 6,346,124 | B1 | 2/2002 | Geiser et al. | 660/450 |
| 6,350,239 | B1 | 2/2002 | Ohad et al. | 600/437 |
| 6,359,190 | B1 | 3/2002 | Ter-Ovanesyan et al. | 604/361 |
| 6,360,027 | B1 | 3/2002 | Hossack et al. | 382/294 |
| 6,375,616 | B1 | 4/2002 | Soferman et al. | 600/443 |
| 6,400,848 | B1 | 6/2002 | Gallagher | 382/254 |
| 6,402,762 | B2 | 6/2002 | Hunter et al. | 606/130 |
| 6,406,431 | B1 | 6/2002 | Barnard et al. | 600/443 |
| 6,409,665 | B1 | 6/2002 | Scott et al. | 600/437 |
| 6,440,071 | B1 | 8/2002 | Slayton et al. | 600/437 |
| 6,440,072 | B1 | 8/2002 | Schuman et al. | 600/437 |
| 6,443,894 | B1 | 9/2002 | Sumanaweera et al. | 600/443 |
| 6,468,218 | B1 | 10/2002 | Chen et al. | 600/443 |
| 6,485,423 | B2 | 11/2002 | Angelsen et al. | |
| 6,491,631 | B2 | 12/2002 | Chiao et al. | 600/443 |
| 6,494,841 | B1 | 12/2002 | Thomas et al. | |
| 6,503,204 | B1 | 1/2003 | Sumanaweera et al. | 600/459 |
| 6,511,325 | B1 | 1/2003 | Lalka et al. | 434/272 |
| 6,511,426 | B1 | 1/2003 | Hossack et al. | 600/437 |
| 6,511,427 | B1 | 1/2003 | Sliwa, Jr. et al. | 600/438 |
| 6,515,657 | B1 | 2/2003 | Zanelli | 345/419 |
| 6,524,249 | B2 | 2/2003 | Moehring et al. | 600/438 |
| 6,535,759 | B1 | 3/2003 | Epstein et al. | 600/547 |
| 6,540,679 | B2 | 4/2003 | Slayton et al. | 600/439 |
| 6,544,179 | B1 | 4/2003 | Schmiesing et al. | 600/447 |

| | | | |
|---|---|---|---|
| 6,545,678 B1 | 4/2003 | Ohazama | 345/427 |
| 6,551,246 B1 | 4/2003 | Ustuner et al. | |
| 6,565,512 B1 | 5/2003 | Ganguly et al. | 600/449 |
| 6,569,097 B1 | 5/2003 | McMorrow et al. | 600/437 |
| 6,569,101 B2 | 5/2003 | Quistgaard et al. | 600/459 |
| 6,575,907 B1 | 6/2003 | Soferman et al. | 600/438 |
| 6,585,647 B1 * | 7/2003 | Winder | 600/437 |
| 6,610,013 B1 | 8/2003 | Fenster et al. | 600/439 |
| 6,611,141 B1 | 8/2003 | Schulz et al. | 324/226 |
| 6,622,560 B2 | 9/2003 | Song et al. | |
| 6,628,743 B1 | 9/2003 | Drummond et al. | 378/8 |
| 6,643,533 B2 | 11/2003 | Knoplioch et al. | 600/407 |
| 6,650,927 B1 | 11/2003 | Keidar | 600/424 |
| 6,676,605 B2 | 1/2004 | Barnard et al. | 600/449 |
| 6,682,473 B1 | 1/2004 | Matsuura et al. | 600/29 |
| 6,688,177 B2 | 2/2004 | Wiesauer | 73/618 |
| 6,695,780 B1 | 2/2004 | Nahum et al. | 600/437 |
| 6,705,993 B2 | 3/2004 | Ebbini et al. | |
| 6,716,175 B2 | 4/2004 | Geiser et al. | 600/450 |
| 6,752,762 B1 | 6/2004 | DeJong et al. | |
| 6,755,787 B2 | 6/2004 | Hossack et al. | 600/447 |
| 6,768,811 B2 | 7/2004 | Dinstein et al. | 382/128 |
| 6,780,152 B2 | 8/2004 | Ustuner et al. | 600/443 |
| 6,788,620 B2 | 9/2004 | Shiraishi et al. | 367/152 |
| 6,801,643 B2 | 10/2004 | Pieper | 382/128 |
| 6,822,374 B1 | 11/2004 | Smith et al. | 310/334 |
| 6,825,838 B2 | 11/2004 | Smith et al. | 345/419 |
| 6,831,394 B2 | 12/2004 | Baumgartner et al. | 310/334 |
| 6,868,594 B2 | 3/2005 | Gururaja | 29/25.35 |
| 6,884,217 B2 | 4/2005 | McMorrow et al. | 600/443 |
| 6,903,813 B2 | 6/2005 | Jung et al. | 356/73 |
| 6,905,467 B2 | 6/2005 | Bradley et al. | 600/443 |
| 6,905,468 B2 | 6/2005 | McMorrow et al. | 600/443 |
| 6,911,912 B2 | 6/2005 | Roe | 340/573.1 |
| 6,936,009 B2 | 8/2005 | Venkataramani et al. | 600/459 |
| 6,939,301 B2 | 9/2005 | Abdelhak | 600/437 |
| 6,951,540 B2 | 10/2005 | Ebbini et al. | 600/437 |
| 6,954,406 B2 | 10/2005 | Jones | 367/152 |
| 6,961,405 B2 | 11/2005 | Scherch | 378/65 |
| 6,962,566 B2 | 11/2005 | Quistgaard et al. | 600/437 |
| 6,970,091 B2 | 11/2005 | Roe | 340/573.1 |
| 7,004,904 B2 | 2/2006 | Chalana et al. | 600/443 |
| 7,025,725 B2 | 4/2006 | Dione et al. | 600/443 |
| 7,041,059 B2 | 5/2006 | Chalana et al. | 600/437 |
| 7,042,386 B2 | 5/2006 | Woodford et al. | 342/25 |
| 7,087,022 B2 | 8/2006 | Chalana et al. | 600/449 |
| 7,141,020 B2 | 11/2006 | Poland et al. | 600/447 |
| 7,142,905 B2 | 11/2006 | Slayton et al. | 600/427 |
| 7,177,677 B2 | 2/2007 | Kaula et al. | 600/546 |
| 7,189,205 B2 | 3/2007 | McMorrow et al. | 600/437 |
| 7,215,277 B2 | 5/2007 | Woodford et al. | 342/25 F |
| 7,255,678 B2 | 8/2007 | Mehi et al. | 600/446 |
| 7,301,636 B2 | 11/2007 | Jung et al. | 356/402 |
| 7,382,907 B2 | 6/2008 | Luo et al. | 382/128 |
| 7,450,746 B2 | 11/2008 | Yang et al. | 382/131 |
| 7,520,857 B2 | 4/2009 | Chalana et al. | 600/446 |
| 7,611,466 B2 | 11/2009 | Chalana et al. | 600/443 |
| 2001/0031920 A1 | 10/2001 | Kaufman et al. | 600/431 |
| 2002/0005071 A1 | 1/2002 | Song et al. | |
| 2002/0016545 A1 | 2/2002 | Quistgaard et al. | 600/437 |
| 2002/0072671 A1 | 6/2002 | Chenal et al. | 600/450 |
| 2002/0102023 A1 | 8/2002 | Yamauchi | |
| 2002/0133075 A1 | 9/2002 | Abdelhak | 600/443 |
| 2002/0147399 A1 | 10/2002 | Mao | |
| 2002/0165448 A1 | 11/2002 | Ben-Haim et al. | 600/424 |
| 2003/0055336 A1 | 3/2003 | Buck et al. | 600/453 |
| 2003/0142587 A1 | 7/2003 | Zeitzew | 367/134 |
| 2003/0174872 A1 | 9/2003 | Chalana et al. | 382/128 |
| 2003/0181806 A1 | 9/2003 | Medan et al. | 600/411 |
| 2003/0216646 A1 | 11/2003 | Angelsen et al. | 600/437 |
| 2003/0229281 A1 | 12/2003 | Barnard et al. | 600/438 |
| 2004/0006266 A1 | 1/2004 | Ustuner et al. | 600/47 |
| 2004/0024302 A1 * | 2/2004 | Chalana et al. | 600/407 |
| 2004/0034305 A1 | 2/2004 | Song et al. | 600/447 |
| 2004/0054280 A1 | 3/2004 | McMorrow et al. | 600/437 |
| 2004/0076317 A1 | 4/2004 | Roberts | 328/128 |
| 2004/0106869 A1 | 6/2004 | Tepper | 600/443 |
| 2004/0127796 A1 | 7/2004 | Chalana | |
| 2004/0127797 A1 | 7/2004 | Barnard et al. | 600/449 |
| 2004/0267123 A1 | 12/2004 | McMorrow et al. | 600/443 |
| 2005/0135707 A1 | 6/2005 | Turek et al. | 382/294 |
| 2005/0174324 A1 | 8/2005 | Liberty et al. | 345/156 |
| 2005/0193820 A1 | 9/2005 | Sheljaskow et al. | 73/649 |
| 2005/0212757 A1 | 9/2005 | Marvit et al. | 345/156 |
| 2005/0215896 A1 | 9/2005 | McMorrow et al. | 600/437 |
| 2005/0228276 A1 | 10/2005 | He et al. | 600/437 |
| 2005/0240126 A1 | 10/2005 | Foley et al. | 601/2 |
| 2005/0253806 A1 | 11/2005 | Liberty et al. | 345/156 |
| 2006/0025689 A1 | 2/2006 | Chalana et al. | 600/456 |
| 2006/0064010 A1 | 3/2006 | Cannon, Jr. et al. | 600/434 |
| 2006/0078501 A1 | 4/2006 | Goertz et al. | |
| 2006/0079775 A1 | 4/2006 | McMorrow et al. | 600/443 |
| 2006/0111633 A1 | 5/2006 | McMorrow et al. | 600/437 |
| 2006/0235301 A1 | 10/2006 | Chalana et al. | 600/443 |
| 2007/0004983 A1 | 1/2007 | Chalana et al. | 600/443 |
| 2007/0232908 A1 | 10/2007 | Wang et al. | 600/437 |
| 2007/0276247 A1 | 11/2007 | Chalana et al. | 600/447 |
| 2007/0276254 A1 | 11/2007 | Yang et al. | 600/463 |
| 2008/0139938 A1 | 6/2008 | Yang et al. | 600/445 |
| 2008/0146932 A1 | 6/2008 | Chalana et al. | 600/447 |
| 2008/0242985 A1 | 10/2008 | Chalana et al. | 600/443 |
| 2008/0249414 A1 | 10/2008 | Yang et al. | 600/445 |
| 2008/0262356 A1 | 10/2008 | Chalana et al. | 600/447 |
| 2009/0062644 A1 | 3/2009 | McMorrow et al. | 600/437 |
| 2009/0088660 A1 | 4/2009 | McMorrow et al. | 600/546 |
| 2009/0105585 A1 | 4/2009 | Wang et al. | 600/437 |
| 2009/0112089 A1 | 4/2009 | Barnard et al. | 600/443 |
| 2009/0264757 A1 | 10/2009 | Yang et al. | 600/443 |

FOREIGN PATENT DOCUMENTS

| | | |
|---|---|---|
| EP | 1 030 187 | 8/2000 |
| EP | 1 076 318 | 2/2001 |
| EP | 2391625 A | 2/2004 |
| JP | 7-171149 | 7/1995 |
| JP | 2000-126178 | 5/2000 |
| JP | 2000-126181 | 5/2000 |
| JP | 2000-126182 | 5/2000 |
| JP | 2000-210286 | 8/2000 |
| WO | 01/35339 | 5/2001 |
| WO | 2009/032778 | 3/2009 |

OTHER PUBLICATIONS

Baker, A., et al., "Prediction of Non-Linear Propagation in Water Due to Diagnostic Medical Ultrasound Equipment", Phys. Med Biol., vol. 36, No. 11, pp. 1457-1464, 1991.

Barentsz et al., "Primary Staging of Urinary Bladder Carcinoma: the Role of MRI and a Comparison with CT," European Radiology vol. 6, pp. 129-133, 1996.

Besl, P., et al., "A Method for Registration of 3-D Shapes," IEEE Transaction on Pattern Analysis and Machine Intelligence, vol. 14, No. 2, pp. 239-256, Feb. 1992.

Birnholz, J., et al., "Amniotic Fluid Accumulation in the First Trimester," American Institute of Ultrasound in Medicine, Journal Ultrasound Medicine, vol. 14, pp. 597-602, 1995.

Bishop, S., et al., "Human Tissue-Temperature Rise During Ultrasound Treatments with the Aquaflex Gel Pad." Journal of Athletic Training, vol. 39, No. 2, pp. 126-131, 2004.

Bouakaz, A., et al., "Noninvasive Bladder Volume Measurements Based on Nonlinear Wave Distortion," Ultrasound in Medicine & Biology, vol. 30, No. 4, pp. 469-476, 2004.

Boyle, P., et al, "Prostate Volume Predicts Outcome of Treatment of Benign Prostatic Hyperplasia with Finasteride: Meta-Analysis of Randomized Clinical Trials," Urology, vol. 48, No. 3, pp. 398-405, 1996.

Cascione, C., et al., "Transabdominal Ultrasound Versus Excretory Urography in Preoperative Evaluation of Patients with Prostatism," The Journal of Urology, vol. 137, pp. 883-885, May 1987.

Chamberlain, P., "Amniotic Fluid Volume: Ultrasound Assessment and Clinical Significance," Seminars in Perinateology, vol. 9, No. 4, pp. 163-167, 1985.

Chamberlain, P. "Ultrasound Evaluation of Amniotic Fluid Volume," American Journal of Obstetrics and Gynaecology, vol. 150, No. 3, pp. 250-254, Oct. 1, 1984.

Cheng, X. et al., "Boundary Extraction Method for Three Dimensional Ultrasonic Echo Imaging Using Fuzzy Reasoning and Relaxation Techniques," IEEE, pp. 1610-1614, 1994.

Christensen, M., et al., "Clinical Manifestations of Benign Prostatic Hyperplasia and Indications for Therapeutic Intervention," Benign Prostatic Hyperplasia, Urologic Clinics of North America, vol. 17, No. 3, pp. 509-516, Aug. 1990.

Crowley, P., et al., "The Value of Ultrasound Measurement of Amniotic Fluid Volume in the Management of Prolonged Pregnancies," British Journal of Obstetrics and Gynaecology, vol. 91, pp. 444-448, May 1984.

Cvitkovic-Kuzmic, A., et al., "Sonographic Measurement of Detrusor Muscle Thickness in Healthy Children," Pedatric Nephrology, vol. 16, pp. 1122-1125, 2001.

Cvitkovic-Kuzmic, A., et al., "Ultrasound Assessment of Detrusor Muscle Thickness in Children with Non-Neuropathic Bladder/Sphincter Dysfunction," European Urology, Vo. 41, pp. 214-219, 2002.

Elliott, P., "Interactive Image Segmentation for Radiation Treatment Planning," IBM Systems Journal, vol. 31, No. 4, pp. 620-634, 1992.

Forbes, F., et al., "Bayesian Morphology: Fast Unsupervised Bayesian Image Analysis," Journal of the American Statistical Association, vol. 94, No. 446, pp. 555-568, Jun. 1999.

Gerald, C., et al., "Applied Numerical Analysis," Fifth Edition, Addison-Wesley Publishing Company, Chapter 3, 'Interplation and Curve Fitting,', pp. 210-287, 1994.

Gobbi, D., et al. "Real-Time 3D Ultrasound for Intraoperative Surgical Guidance," 8 pgs, 2001.

Gramellini, D., et al., "Sonographic Assessment of Amniotic Fluid Volume Between 11 and 24 Weeks of Gestation: Construction of Reference Intervals Related to Gestational Age," Ultrasound Obstetrics Gynaecology, vol. 17, pp. 410-415, 2001.

Grover, J., et al., "Three-Dimensional Method for Determination of Amniotic Fluid Volume in Intrauterine Pockets," vol. 90, No. 6, pp. 1007-1010, Dec. 1997.

Hakenberg, O., et al., "Bladder Wall Thickness in Normal Adults and Men with Mild Lower Urinary Tract Symptoms and Benign Prostatic Enlargement," Neurourology and Urodynamics, vol. 19, pp. 585-593, 2000.

Hakenberg, O., et al., "The Estimation of Bladder Volume by Sonocystrography," Journal of Urology, vol. 130, No. 2, pp. 249-251, Aug. 1983.

Hamilton, M., et al., "Nonlinear Acoustics," Copyright 1998 by Academic Press, Chapter 4, 'Progressive Waves in Lossless and Lossy Fluids,' pp. 65-150.

Holmes, J., et al., "Ultrasonic Studies of the Bladder," The Journal of Urology, vol. 91, pp. 654-663, 1967.

Jeng, C., et al., "Amniotic Fluid Index Measurement with the Four-Quadrant Technique During Pregnancy," The Journal of Reproductive Medicine, Inc., vol. 35, No. 7, pp. 674-677, Jul. 1990.

Jequier, S., et al., "Sonographic Measurements of the Normal Bladder Wall in Children," AJR, vol. 149, pp. 563-566, Sep. 1987.

Jong, et al., "Ultrasound Contrast Agents" ISBN 1-85317-858-4 chapter 3 "Contrast-Specific Imaging Methods", 2003.

Khullar, V., et al. "A Novel Technique for Measuring Bladder Wall Thickness in Women Using Transvaginal Ultrasound,"Ultrasound Obestetrics and Gynaecology, vol. 4, pp. 220-223, 1994.

Khullar, V., et al., "Ultrasound: a Noninvasive Screening Test for Detrusor Instability," British Journal of Obstetrics and Gynaecology, vol. 103, pp. 904-908, Sep. 1996.

Kojima, M., et al., "Reversible Change of Bladder Hypertrophy Due to Benign Prostatic Hyperplasia After Surgical Relief of Obstruction," The Journal of Urology, vol. 158, pp. 89-93, Jul. 1997.

Kojima, M., et al., "Ultrasonic Estimation of Bladder Weight as a Measure of Bladder Hypertrophy in Men with Infravesical Obstruction: a Preliminary Report," Urology, vol. 47, No. 6, pp. 942-947, 1996.

Krenning, B., et al., "Assessment of Left Ventricular Function by Three-Dimensional Echocardiography," Cardiovascular Ultrasound, 7 pgs., 2003.

Kruczkowski et al., "A Non-Invasive Ultrasonic System to Determine Residual Bladder Volumes", IEEE Engineering in Medicine Biology Society 10th Ann Conf, pp. 1623-1624, 1988.

Lea, J., et al., "Registration and Immobilization in Robot-Assisted Surgery," Computer Aided Surgery, vol. 1, No. 2, pp. 80-87, 1995.

Lorensen, W., et al., "Marching Cubes: A High Resolution 3D Surface Construction Algorithm," ACM Siggraph Computer Graphics, vol. 21, No. 4, pp. 163-169, Jul. 1987.

Madsen, F., et al., "Clinical Manifestations of Benign Prostatic Hyperplasia," Advances in Benign Prostatic Hyperplasia, Urologic Clinics of North America, vol. 22, No. 2, pp. 291-298, May 1995.

Magann, E., et al., "Amniotic Fluid Volume Determination," American Journal of Obstetrics and Gyneacology, Vo. 169, No. 2, Part 1, pp. 435-437, 1999.

Magann, E., et al., "Measurement of Amniotic Fluid Volume: Accuracy of Ultrasonography Techniques," American Journal of Obstetrics and Gyneacology, vol. 167, No. 6, pp. 1533-1537, 1992.

Magann, E., et al., "Ultrasound Estimate of Amniotic Fluid Volume: Color Doppler Overdiagnosis of Oligohydramnios," Obstetrics & Gynecology, vol. 98, No. 1, pp. 71-74, Jul. 2001.

Magann, E., et al., "Ultrasound Estamation of Amniotic Fluid Volume Using the Largest Vertical Pocket Containing Umbilical Cord: Measure to or Through the Cord," Ultrasound Obstetrics and Gynecology, vol. 20, pp. 464-467, 2002.

Manieri, C., et al., "The Diagnosis of Bladder Outlet Obstruction in Men by Ultrasound Measurement of Bladder Wall Thickness," The Journal of Urology, vol. 159, 761-765, pp. 761-765, Mar. 1998.

Mann, S., et al., "Novel Technique for Assessing Amniotic Fluid Volume: use of a Three-Dimensional Bladder Scanner," The Journal of Maternal-Fetal Medicine, vol. 9, pp. 308-310, 2000.

Manning, F., et al., "Qualitative Amniotic Fluid Volume Determination by Ultrasound: Antepartum Detection of Intrauterine Growth Retardation," American Journal of Obstetrics and Gynecology, vol. 139, No. 3, pp. 254-258, Feb. 1, 1981.

Martan, A., et al., "Ultrasound Imaging of the Lower Urinary System in Women after Burch Colposuspension," Ultrasound Obstetrics and Gynecology, vol. 17, pp. 58-64, 2001.

Matthews, P. et al., "The Use of Ultrasound in the Investigation of Prostatism," British Journal of Urology, vol. 54, pp. 536-538, 1982.

Merks, E. et al., "Design of a Multilayer Transducer for Acoustic Bladder Volume Assessment," IEEE Transacations on Ultrasonics, Ferroelectrics and Frequency Control, vol. 53, No. 10, pp. 1730-1738, Oct. 2006.

Merks, E., et al., "A KLM-Circuit Model of a Multi-Layer Transducer for Acoustic Bladder Volume Measurements," Ultrasonics, vol. 44, pp. 705-710, Dec. 22, 2006.

Miyashita, H., et al., "Ultrasonic Measurement of Bladder Weight as a Possible Predictor of Acute Urinary Retention in Men with Lower Urinary Tract Symptoms Suggestive of Benign Prostatic Hyperplasia," Ultrasound in Medicine & Biology, vol. 28, No. 8, pp. 985-990, 2002.

Moore, T., "Superiority of the Four-Quadrant Sum Over the Single-Deepest-Pocket Technique in Ultrasonographic Identification of Abnormal Amniotic Fluid Volumes," American Journal of Obstetrics and Gynecology, vol. 163, No. 5, pp. 762-767, 1990.

Muller, L., et al., "Detrusor Thickness in Healthy Children Assessed by a Standardized Ultrasound Method," The Journal of Urology, vol. 166, pp. 2364-2367, Dec. 2001.

Muller, L., et al., "Standardized Ultrasound Method for Assessing Detrusor Muscle Thickness in Children," The Journal of Urology, vol. 164, pp. 134-138, Jul. 2000.

Myles, T., et al., "Four-Quadrant Assessment of Amniotic Fluid Volume: Distribution's Role in Predicting Fetal Outcome," Journal of Obstetrics and Gynecology, vol. 80, No. 5, pp. 769-774, Nov. 1992.

Naya, Y., et al., "Intraobserver and Interobserver Variance in the Measurement of Ultrasound-Estimated Bladder Weight," Ultrasound in Medicine and Biology, vol. 24, No. 5, pp. 771-773, 1998.

Oelke, M., et al., "Increase in Detrusor Wall Thickness Indicates Bladder Outlet Obstuction (BOO) in Men," World Journal of Urology, vol. 19, pp. 443-452, 2002.

Ohashit, G., et al., "Boundary Estimation for Ultrasonic 3-D Imaging," SPIE vol. 1898 Image Processing, pp. 480-486, 1993.

Oomen, JA, et al., "Towards Assessment of Regional Wall Stress of the Left Ventricle Using 3D Ultrasound Imaging," IEEE Computers in Cardiology, vol. 26, pp. 129-132, 1999.

Phelan, J., et al., Amniotic Fluid Volume Assessment with the Four-Quadrant Technique at 36-42 Weeks' Gestation, The Journal of Reproductive Medicine, vol. 32, No. 7, pp. 540-542, Jul. 1987.

Rutherford, S., et al., "The Four-Quadrant Assessment of Amniotic Fluid Volume: An Adjunct to Antepartum Fetal Heart Rate Testing," Journal of Obstetrics and Gynecology, vol. 70, No. 3, Part 1, pp. 353-356, Sep. 1987.

Sagiv, C., et al., "Application of a Semiautomatic Boundary Detection Algorithm for the Assessment of Amniotic Fluid Quantity Form Ultrasound Images," Ultrasound in Medicine and Biology, vol. 25, No. 4, pp. 515-526, 1999.

Sahin, B., et al., "Estimation of the Amniotic Fluid Volume Using the Cavalieri Method on Ultrasound Images," International Journal of Gynecology and Obstetrics, vol. 82, pp. 25-30, 2003.

Santilli, J., et al., "Diagnosis and Treatment of Abdominal Aortic Aneurysms," American Family Physician, vol. 56, No. 4, pp. 1081-1090, Sep. 1997.

Scheinerman, E., "Invitation to Dynamical Systems," Chapter 5, 'Fractals,' Prentice Hall pp. 231-315, 1996.

Schiff, E., et al., "Standardized Measurement of Amniotic Fluid Volume by Correlation of Sonography with Dye Dilution Technique," Obestetrics and Gynecology, vol. 76, No. 1, pp. 44-46, Jul. 1990.

Schrimmer, D., et al., "Sonographic Evaluation of Amniotic Fluid Volume," Clinical Obstetrics and Gynecology, vol. 45, No. 4, pp. 1026-1029, 2002.

Sepulveda W., et al., "Direct Volume Measurement at Midtrimester Amnioinfusion in Relation to Ultrasonographic Indexes of Amniotic Fluid Volume," American Journal of Obstetrics and Gynecology, vol. 170, No. 4, pp. 1160-1163, Apr. 1994.

Shiota, T., et al., "Real-time Three-Dimensional Echocardiography for Determining Right Ventricular Stroke Volume in an Animal Model of Chronic Right Ventricular Volume Overload," Circulation Journal of the American Heart Association, vol. 97, pp. 1897-1900, 1998.

Stangenberg, M., et al., "Amniotic Fluid Volumes in Pregnant Diabetics During the Last Trimester," Acta Obstetrics Gynecology Scand, vol. 61, pp. 313-316, 1982.

Szabo, T., et al., "Effects of Nonlinearity on the Estimation of In Situ Values of Acoustic Output Parameters," Journal of Ultrasound in Medicine, American Institute of of Ultrasound in Medicine, vol. 18, No. 1, pp. 33-41, 1999.

Weissman, A., et al., "Sonographic Measurement of Amniotic Fluid Volume in the First Trimester of Pregnancy," American Institute of Ultrasound in Medicine, vol. 15, pp. 771-774, 1996.

Hamilton; Nonlinear Acoustics; 1998; pp. 65-150. Please see pp. 132-133 regarding the use of Goldberg numbers; Academic Press; San Diego, CA USA.

* cited by examiner

SYSTEMS AND METHODS FOR QUANTIFICATION AND CLASSIFICATION OF FLUIDS IN HUMAN CAVITIES IN ULTRASOUND IMAGES

PRIORITY CLAIM

This application is a continuation in part and claims priority to U.S. patent application Ser. No. 10/523,681 filed Dec. 23, 2005, which claims priority to WIPO application number PCT/EP2003/07807 filed Jul. 1, 2003, which claims priority to UK patent application number GB2391625A filed Aug. 9, 2002.

This application claims priority to and is a continuation-in-part of U.S. patent application Ser. No. 11/119,355 filed Apr. 29, 2005 now U.S. Pat. No. 7,520,857, which claims priority to U.S. provisional patent application Ser. No. 60/566,127 filed Apr. 30, 2004. This application also claims priority to and is a continuation-in-part of U.S. patent application Ser. No. 10/701,955 filed Nov. 5, 2003 now U.S. Pat. No. 7,087,022, which in turn claims priority to and is a continuation-in-part of U.S. patent application Ser. No. 10/443,126 filed May 20, 2003 now U.S. Pat. No. 7,041,059.

This application claims priority to and is a continuation-in-part of U.S. patent application Ser. No. 11/061,867 filed Feb. 17, 2005 U.S. Pat. No. 7,611,466, which claims priority to U.S. provisional patent application Ser. No. 60/545,576 filed Feb. 17, 2004 and U.S. provisional patent application Ser. No. 60/566,818 filed Apr. 30, 2004.

This application claims priority to U.S. provisional patent application 60/633,485 filed Dec. 6, 2004.

This application claims priority to U.S. provisional patent application 60/608,426 filed Sep. 9, 2004 and 60/605,391 filed Aug. 27, 2004.

This application is also a continuation-in-part of and claims priority to U.S. patent application Ser. No. 10/704,996 filed Nov. 10, 2003 now abandoned which claims priority to and is a continuation-in-part of U.S. patent application Ser. No. 10/701,955 filed Nov. 5, 2003 now U.S. Pat. No. 7,087,022 which claims priority to U.S. patent application Ser. No. 10/633,186 filed Jul. 31, 2003 which claims priority to U.S. patent application Ser. No. 10/443,126 filed May 12, 2003, which claims priority to U.S. provisional patent application Ser. No. 60/423,881 filed Nov. 5, 2002 and U.S. provisional patent application Ser. No. 60/400,624 filed Aug. 2, 2002.

This application is also a continuation-in-part of and claims priority to U.S. patent application Ser. No. 10/165,556 filed Jun. 7, 2002 now U.S. Pat. No. 6,676,605.

This application is also a continuation-in-part of and claims priority to PCT application serial number PCT/US03/24368 filed Aug. 1, 2003, which claims priority to U.S. provisional patent application Ser. No. 60/423,881 filed Nov. 5, 2002 and U.S. provisional patent application Ser. No. 60/400,624 filed Aug. 2, 2002.

This application is also a continuation-in-part of and claims priority to PCT Application Serial No. PCT/US03/14785 filed May 9, 2003, which is a continuation of U.S. patent application Ser. No. 10/165,556 filed Jun. 7, 2002 now U.S. Pat. No. 6,676,605.

This application is also a continuation-in-part of and claims priority to U.S. patent application Ser. No. 10/633,186 filed Jul. 31, 2003, now U.S. Pat. No. 7,004,904 which claims priority to U.S. provisional patent application Ser. No. 60/423,881 filed Nov. 5, 2002 and U.S. provisional patent application Ser. No. 60/400,624 filed Aug. 2, 2002, and to U.S. patent application Ser. No. 10/443,126 filed May 20, 2003 which claims priority to U.S. provisional patent application Ser. No. 60/423,881 filed Nov. 5, 2002 and to U.S. provisional application 60/400,624 filed Aug. 2, 2002.

This application also claims priority to U.S. application Ser. No. 11/010,539 filed Dec. 13, 2004, which claims priority to PCT/EP03/07807 filed Jul. 17, 2003, which claims priority to UK Application Serial No. 0218547.8 filed Aug. 9, 2002; and U.S. patent application filed Feb. 3, 2005 via U.S. Postal Service Express Mail number EV510340824US, which claims priority to PCT/EP03/07807 filed Jul. 17, 2003, which claims priority to UK Application Serial No. 0218547.8 filed Aug. 9, 2002.

This application also claims priority to U.S. provisional patent application Ser. No. 60/470,525 filed May 12, 2003, and to U.S. patent application Ser. No. 10/165,556 filed Jun. 7, 2002. All of the above applications are incorporated by reference in their entirety as if fully set forth herein.

FIELD OF INVENTION

This invention relates to ultrasound imaging of bodily tissues, bodily fluids, and fluid-filled cavities.

BACKGROUND OF THE INVENTION

Ultrasound imaging is accomplished by placing an ultrasound transducer on a selected location of a body and projecting ultrasound energy into the body. Acoustic waves reflecting from internal structures in the body are then received by the transducer and are processed to form an image of the internal structures. In a particular ultrasound method, amplitudes of selected harmonics of the returned signal are processed to form the ultrasound image. Briefly and in general terms, harmonic generation by the internal structures in the body is at least partially determined by the properties of the tissue that reflect the ultrasound energy, so that the presence of harmonics in the received echo may be used to generate useful information in the ultrasound image, as discussed in further detail in A. Bouakaz, E. Merks, C. Lancee, N. Bom, "*Noninvasive Bladder Volume Measurements Based on Nonlinear Wave Distortions*," Ultrasound in Medicine & Biology, 30:4, pp. 469-476, which publication is incorporated by reference herein.

In selected ultrasound imaging applications, it is often desirable to distinguish between a bodily fluid and an adjacent tissue, or between bodily fluids of different types, such as between blood and various other bodily fluids. For example, when a selected anatomical portion is imaged using B-mode ultrasound imaging, a bodily fluid and certain adjacent soft tissues within the selected portion may be relatively indistinguishable in the resulting image. Moreover, when blood within the selected portion and other bodily fluids are imaged using B-mode ultrasound, images may be generated that similarly fail to properly distinguish the blood from the other bodily fluids.

Accordingly, a new imaging system is needed that permits the diagnostician to easily distinguish or discriminate between different fluid compositions, or between a bodily fluid and tissue. It is further desirable to render more easily detectable in an ultrasound image any boundaries between cavities that contain fluids of different composition, and between a bodily fluid and a bodily tissue.

SUMMARY

The present invention comprises ultrasound imaging systems and methods. In one aspect, an ultrasonography method includes creating a database that is representative of a tissue, a fluid, or a cavity of a body, and transmitting ultrasound pulses into a region-of-interest in a patient. Echoes are received from the region of interest, and based upon the received echoes, compiling an ultrasonic pattern of the region-of-interest is compiled. The pattern is processed by comparing the region-of-interest patterns to the pattern information stored in the database. A composition within the region-of-interest of the patient is then determined.

BRIEF DESCRIPTION OF THE DRAWINGS

The embodiments of the present invention are described in detail below with reference to the following drawings.

DETAILED DESCRIPTION OF THE PREFERRED EMBODIMENTS

The present invention relates to the ultrasound imaging of tissues and/or fluid-filled cavities having linear or non-linear acoustic properties. Many specific details of certain embodiments of the invention are set forth in the following description and in FIGS. 1 through 21 to provide a thorough understanding of such embodiments. One skilled in the art, however, will understand that the present invention may have additional embodiments, or that the present invention may be practiced without several of the details described in the following description.

Figure 1:
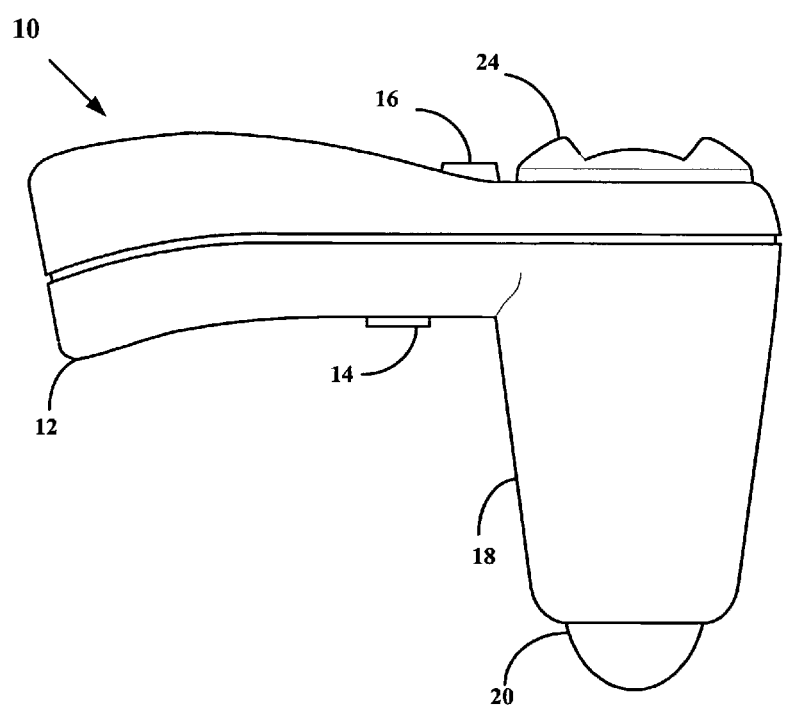
FIG. 1 is a side elevational view of a microprocessor-controlled transceiver according to an embodiment of the invention.

FIG. 1 is a side elevational view of an ultrasound transceiver 10 according to an embodiment of the invention. The transceiver 10 includes a transceiver housing 18 having an outwardly extending handle 12 that is suitably configured to allow a user to manually manipulate the transceiver 10. The handle 12 includes a trigger 14 that allows the user to initiate an ultrasound scan of a selected anatomical portion, and a cavity selector 16, which will be described in greater detail below. The transceiver 10 also includes a transceiver dome 20 that contacts a surface portion of the patient when the selected anatomical portion is scanned, and a display 24 operable to view processed results from the ultrasound scan, and to allow operational interaction between the user and the transceiver 10. Accordingly, the display 24 may be configured to display alphanumeric data that indicates a proper and/or optimal position of the transceiver 10 relative to the selected anatomical portion. In other embodiments, two- or three-dimensional images of the selected anatomical region may be displayed on the display 24. The display 24 may be a liquid crystal display (LCD), a light emitting diode (LED) display, a cathode ray tube (CRT) display, or other suitable display devices operable to present alphanumeric data and/or graphical images to a user.

The transceiver 10 further includes a microprocessor (not shown in FIG. 1) and computational algorithms (also not shown in FIG. 1) that cooperatively provide enhanced ultrasound harmonic imaging that permits boundaries between different fluid compositions to be distinguished. In addition, the transceiver 10 may be suitably configured to distinguish between a bodily fluid and tissue, between dissimilar tissues, and/or between dissimilar bodily organs. The computational algorithms will be discussed in greater detail below. The transceiver 10 may also be coupled to a computer system (not shown in FIG. 1) that is operable to receive either digital or analog signals from the transceiver 10 and to process the signals to generate a desired ultrasound image. In addition, the computer system may also at least partially control the operation of the transceiver 10. The computer system may comprise any microprocessor-based computer or other computer systems, such as a mainframe that is capable of executing operating instructions and manipulating data. Accordingly, the computer system is not limited to a typical desktop or laptop computer device.

The operation of the transceiver 10 will now be described. The transceiver dome 20 of the transceiver 10 is positioned against a surface portion of a patient that is proximate to the anatomical portion to be scanned. The user then actuates the transceiver 10 by depressing the trigger 14. In response, the transceiver 10 transmits ultrasound signals into the body, and receives corresponding return echo signals that are at least partially processed by the transceiver 10 to generate an ultrasound image of the selected anatomical portion. In a particular embodiment, the transceiver 10 transmits ultrasound signals in a range that extends from approximately about two megahertz (MHz) to approximately about ten MHz.

Still referring to FIG. 1, the cavity selector 16 is structured to adjustably control the transmission and reception of ultrasound signals to the anatomy of a patient. In particular, the cavity selector 16 adapts the transceiver 10 to accommodate various anatomical details of male and female patients. For example, when the cavity selector 16 is adjusted to accommodate a male patient, the transceiver 10 is suitably configured to locate a single cavity, such as a urinary bladder in the male patient. In contrast, when the cavity selector 16 is adjusted to accommodate a female patient, the transceiver 10 is configured to image an anatomical portion having multiple cavities, such as a bodily region that includes a bladder and a uterus. Alternate embodiments of the transceiver 10 may include a cavity selector 16 that is configured to select a single cavity scanning mode, or a multiple cavity-scanning mode that may be used with male and/or female patients. The cavity selector 16 may thus permit a single cavity region to be imaged, or a multiple cavity region, such as a region that includes a lung and a heart to be imaged.

Figure 2:
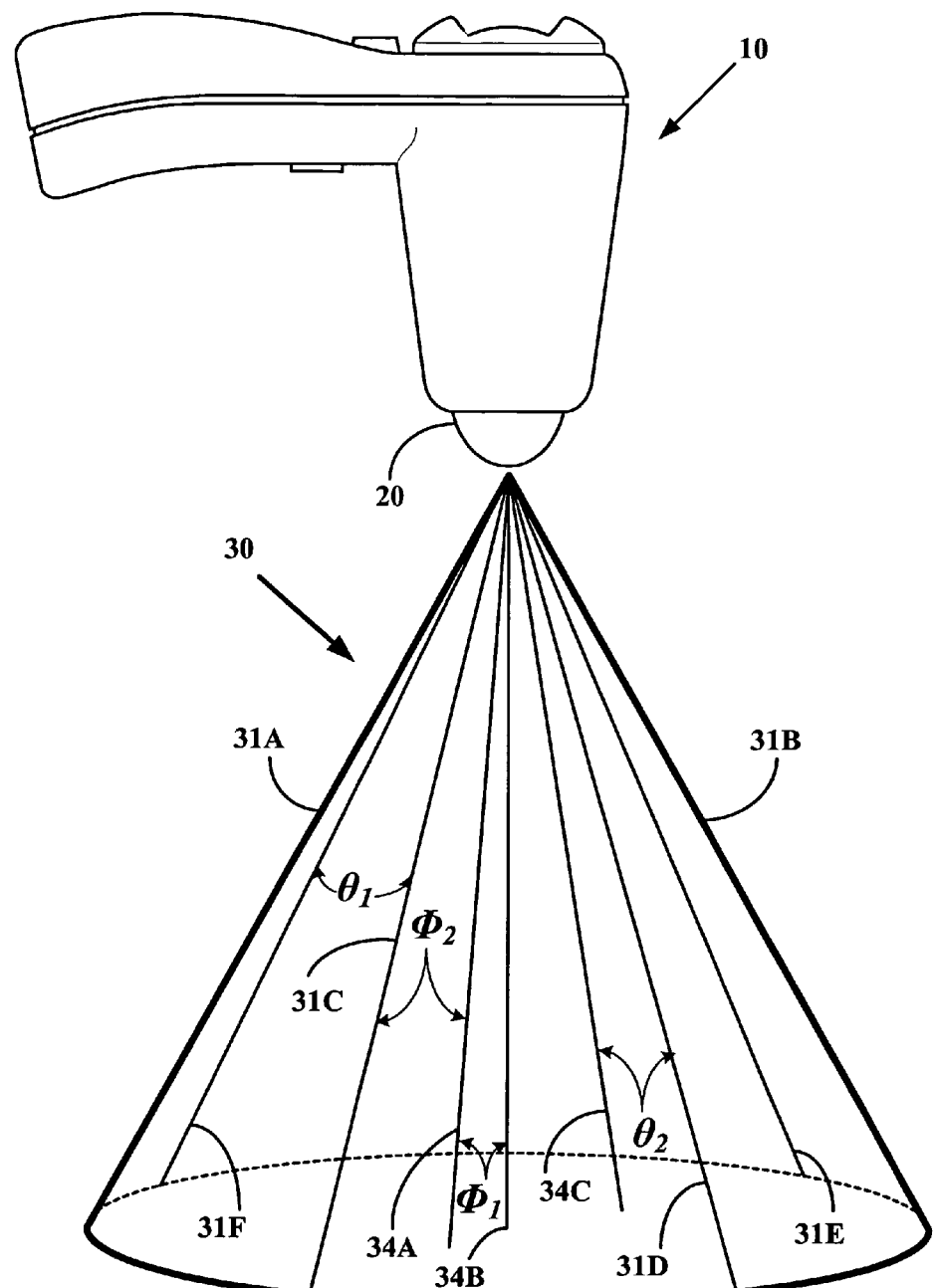
FIG. 2 is a representation of an ultrasound scan cone emanating from the transceiver in a conic shape formed by a plurality of three-dimensional distributed scan lines.

FIG. 2 is a representation of an ultrasound scan cone 30 emanating from the transceiver 10 of FIG. 1 that will be used to further describe the operation of the transceiver 10. The scan cone 30 has a substantially conic shape formed by a plurality of three-dimensional distributed scan lines. A scan cone 30 is shown emanating from the dome 20 of the transceiver 10 in encompassing a plurality of three-dimensional-distributed scan lines 31A-34E. The plurality of scan lines 31A-34E represent a line array in three-dimensional space. The scan lines within the line array are one-dimensional ultrasound A-lines that emanate from the transceiver 10 at different coordinate directions that taken as an aggregate form the scan cone 30. The different coordinate directions comprise a length r of a given scan line, and a rotational angle $\theta$ and a tilt angle $\phi$. Thus, one or more points P along a scan line within the line array 31A-34E are defined by the distance r and the angular coordinates $\phi$, and $\theta$.

The plurality of three-dimensional distributed scan lines 31A-34E comprises a plurality of peripheral scan lines 31A-E and a plurality of internal scan lines 34A-D. The three-dimensional-distributed A-lines (scan lines) are not necessarily confined within a scan plane, but instead are directed to sweep throughout the internal regions and along the periphery of the scan cone 30. The three-dimensional-distributed scan lines not only would occupy a given scan plane in a three-dimensional array of two-dimensional scan planes, but also the inter-scan plane spaces, from the conic axis to and including the conic periphery. For example, assume line 34 B is a conical axis line and lines 31C and 34A are coplanar with line 34B. Lines 34A and 34B are separated by a tilt angle $\phi_1$ and lines 31C and 34A are separated by a tilt angle $\phi_2$. Similarly, lines 31F and 31C are separated by a rotational angle $\theta_1$ and lines 31D and 34C are separated by a rotational angle $\theta_2$.

The internal scan lines are represented by scan lines 34A-C. The number and location of the internal scan lines emanating from the transceiver 10 is variable and may be selected to sufficiently visualize structures within the scan cone 30. The internal scan lines are not peripheral scan lines. The peripheral scan lines 31A-F occupy the conic periphery and converge near the apex of the scan cone 30, thus representing the peripheral limits of the scan cone 30.

Figures 3A, 3B:
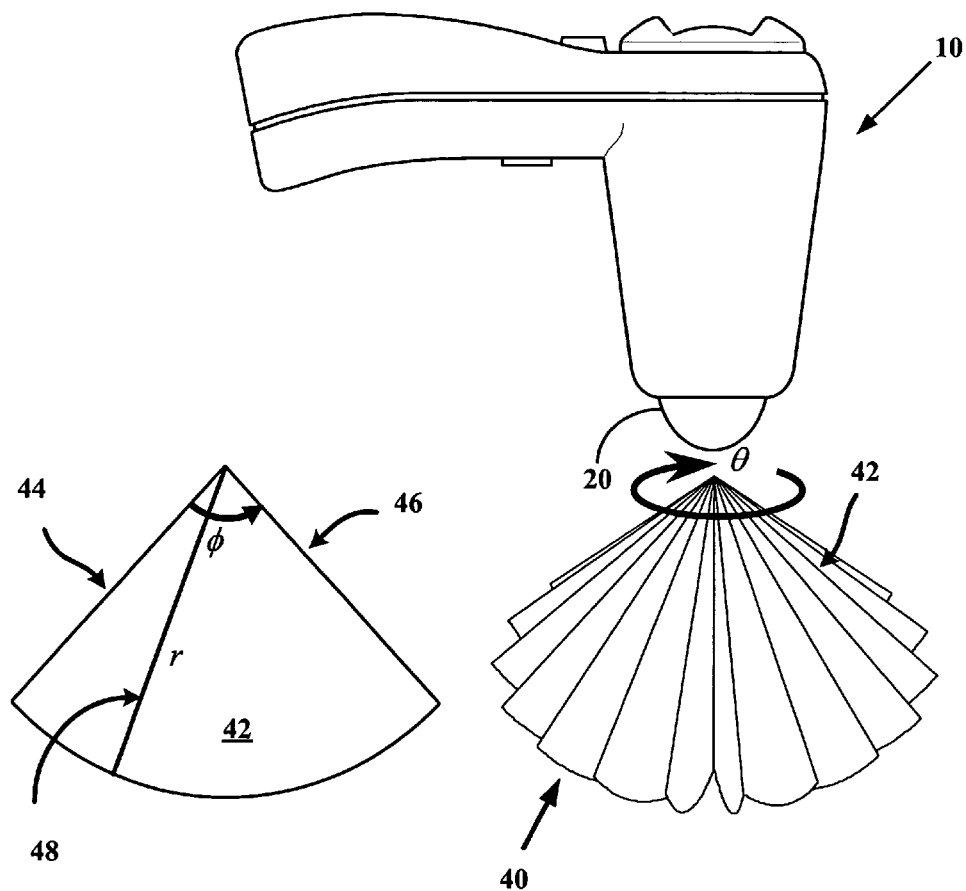
FIG. 3A is a representation of an ultrasound scan cone emanating from the transceiver in a conic shape formed by a rotational array of two-dimensional scan planes.
FIG. 3B is a representation of a scan plane of the rotational array.

FIG. 3A is a representation of an ultrasound scan cone emanating from the transceiver in a conic shape formed by a rotational array of two-dimensional scan planes. The scan cone 40 emanating from the dome 20 includes a plurality of scan planes 42 assembled as a rotational array. The scan planes within the rotational array are angularly separated by an angle $\theta$.

FIG. 3B is a representation of the scan plane of the rotational array. A scan plane 42 is formed by a scan line 48 that rotationally pivots between a first leg 44 and a second leg 46 about a pivot angle $\phi$. The depth of the scan plane 42 is determined by the effective length r of the scan line 48. The area of the scan plane 42 is determined as a product of the length r of the scan line 48 and region swept by the scan line 48 as it migrates about pivot angle $\phi$ between the first and second legs 44 and 46.

Figure 4:
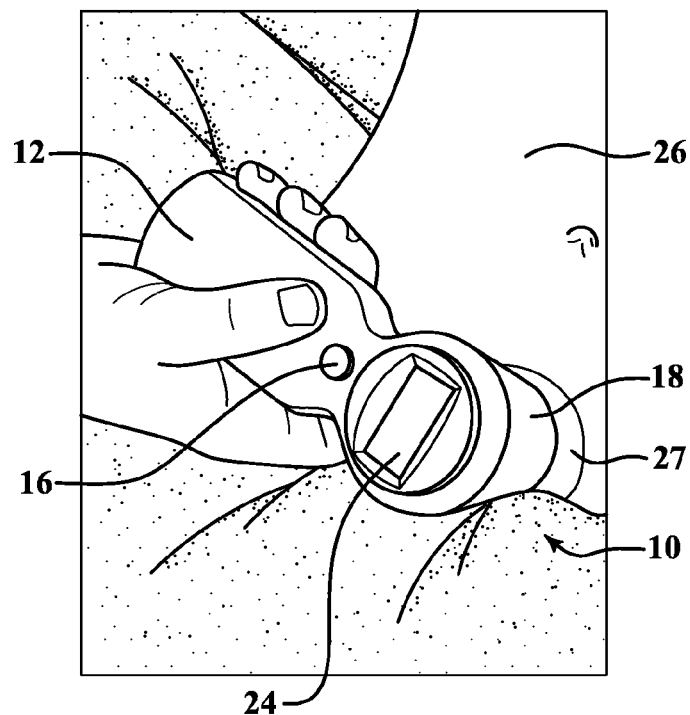
FIG. 4 is a is a depiction of the hand-held transceiver in use for scanning the abdominal area of a patient.

FIG. 4 is an isometric view of the transceiver 10 positioned on an external portion of a patient 26 that will be used to describe a method of data acquisition for identifying fluids in bodily cavities according to an embodiment of the invention. The transceiver 10 is positioned against a surface portion of the patient 26, and a targeting phase is initiated. In a particular embodiment, the transceiver 10 is then operated in a two-dimensional continuous acquisition mode, which permits data to be continuously acquired and presented as a discrete scan plane image on the display 24 (or another external display device) as the operator physically moves the transceiver 10 across various external portions of the patient 26. In this embodiment, the operator moves the transceiver 10 around an abdominal region and depresses the trigger 14 of the transceiver 10 to continuously acquire real-time two-dimensional images that may be continuously viewed on the display 24, or on another display device. For example, when an anatomical portion that contains a urinary bladder is imaged, urine confined within the bladder appears as a dark region, and a urine fluid area may be calculated. An alphanumeric indication of the urine fluid area (for example, in $cm^2$) may also be calculated and visually presented on the display 24. Similarly, if the patient 26 is a pregnant female, amniotic fluid within the uterus may also be imaged and a corresponding amniotic fluid area may be calculated and displayed on the display 24. After acquisition of the two dimensional measurements, the volume of urine and amniotic fluids are measured in the respective bladder and uterus by acquiring a 3-D scan as a multiple scan plane array similar to the scan cone 40. Alternatively, if the two-dimensional measurements are acquired as three-dimensional distributed scan lines, a three-dimensional scan is accomplished as a three-dimensional scan cone of three-dimensional distributed scan lines similar to the scan cone 30. A cavity selector 16 (as shown in FIG. 1) is engaged to detect and measure the volumes of either single or multiple cavities in a subject. In a particular embodiment where the transceiver 10 is positioned over the symphasis pubis for acquisition of three-dimensional ultrasound images, a single cavity includes one of the bladder and the uterus, and a multiple cavity includes the bladder and the uterus.

Figure 5:
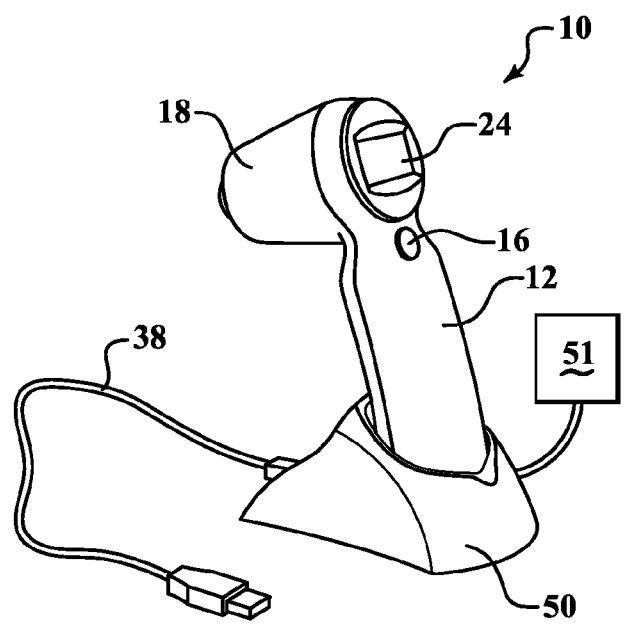
FIG. 5 is a perspective view of the hand-held transceiver device sitting in a communication cradle.

FIG. 5 is an isometric view of transceiver 10 according to another embodiment of the invention. The transceiver 10 is structured to be received by a support cradle 50. The support cradle 50 is coupled to a power supply 51 that provides electrical energy to the cradle 50 that is communicated to the transceiver 10 either conductively or inductively to provide a charging current to a power supply positioned within the transceiver 10. The support cradle 50 is also configured to receive ultrasound data from the transceiver 10 when positioned in the cradle 50, which may be transferred to an external processor (not shown in FIG. 3) through a digital communications link 38, such as a link that employs a universal serial bus (USB), a FIREWIRE bus in conformity with IEEE-1394, an RS-232 compatible link, or other similar communications links in conformity with still other protocols. In other embodiments, the communications link 38 may be a wireless link, such as wireless local area network (LAN) or a wireless wide area network (WAN). Alternatively, the cradle 50 may be powered by the link 38.

The communications link 38 may also advantageously provide a means for transferring imaging data from the transceiver 10, and for transferring software updates or software revisions from the external processor to the transceiver 10. In a particular embodiment, the cradle 50 may include a memory device operable to retain digital data received from the transceiver 10 before the data is transferred to the external processor through the communications link 38.

Figure 5B:
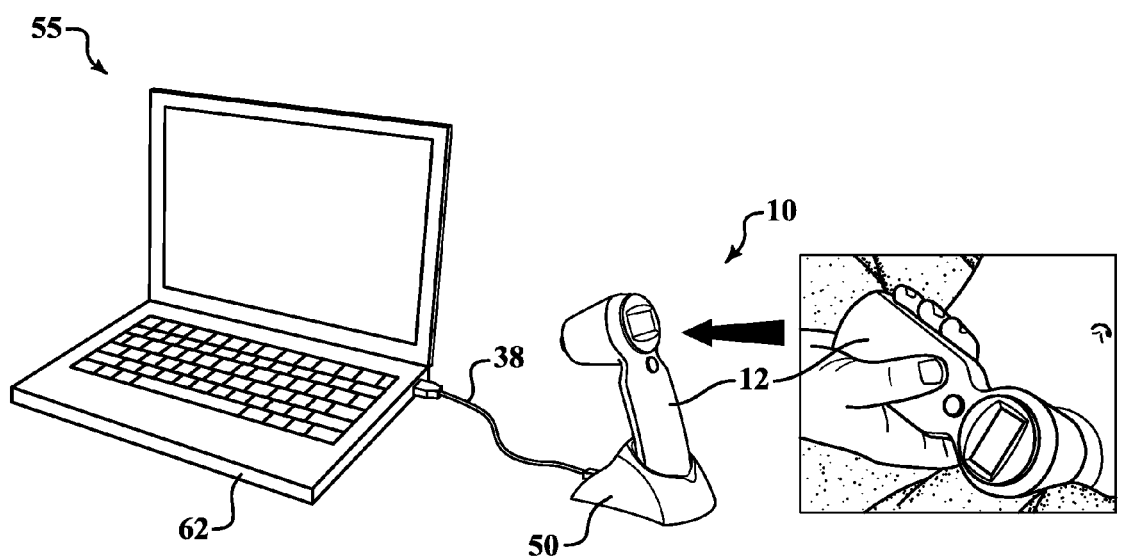
FIG. 5B illustrates a schematic view of an imaging system.

FIG. 5B illustrates a schematic view of an imaging system 55. The imaging system 55 includes the transceiver 10 positioned in the supporting cradle 50. The communications link 38 connects the transceiver 10 housed in the cradle 12 with a computer 62. The computer 62 may be a desktop, laptop, or other microprocessor-based portable computing device. Data from the transceiver 10 is routed through the cradle 50 to the computer 62 via the communications link 38. The communications link 38 may be a conductive link, as shown in FIG. 5B, or it may be a wireless radio frequency link or an optical link, such as a wireless infrared link. Within the computer 62 are executable programs to implement the algorithms of the particular embodiments, including the processing of ultrasound signals, retrieving imaging programs, and instructions to perform ultrasound enhancement procedures. Various ultrasound images are developed by processing the ultrasound signal data, including one-dimensional ultrasound images, two-dimensional images, three-dimensional renderings, and enhanced images from the retrieved imaging programs and instructions. The generated images may be stored within the computer 62.

Figure 6:
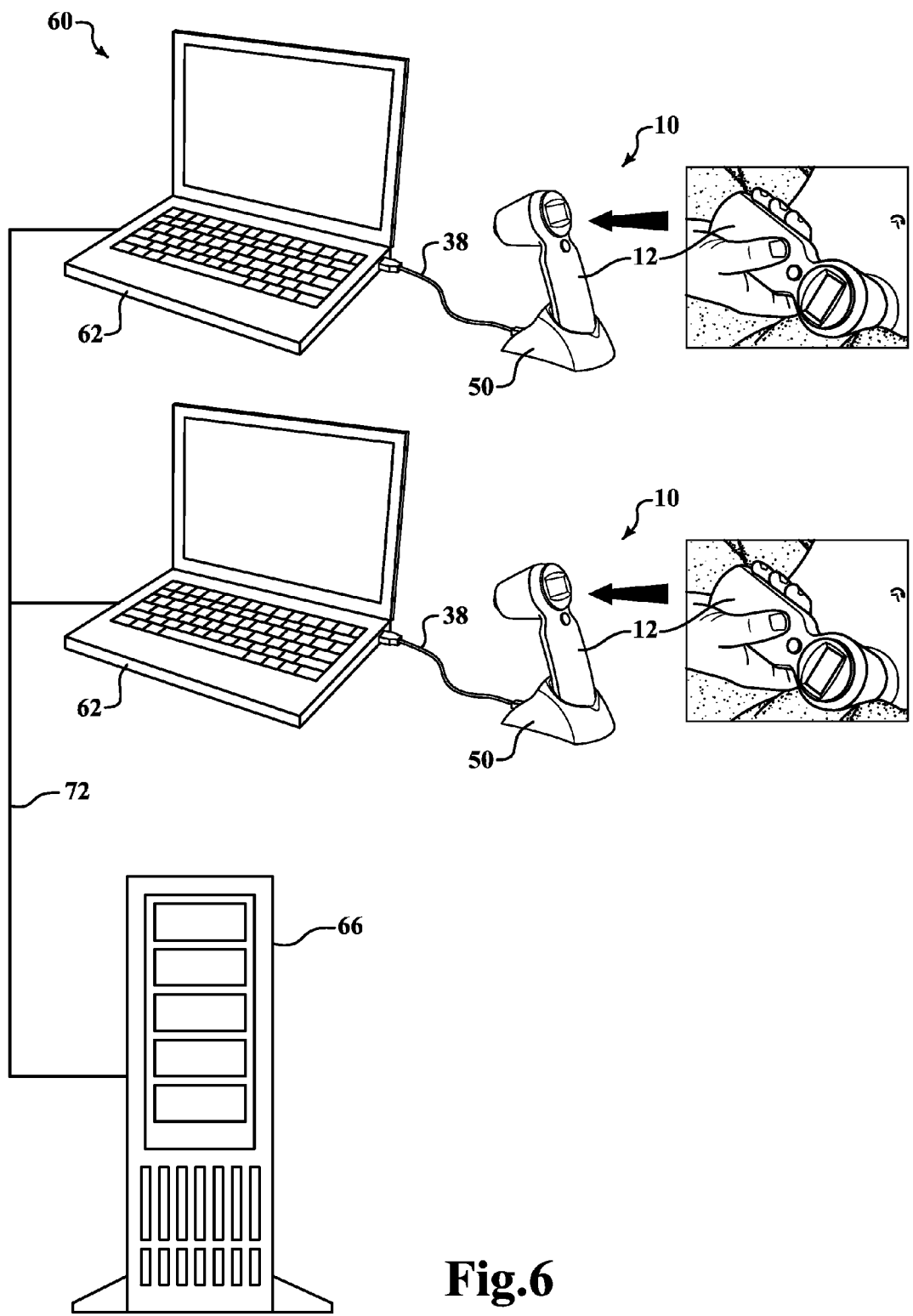
FIG. 6 depicts a schematic view of a plurality of transceivers in connection with a server.

FIG. 6 is a partial isometric and diagrammatic view of a networked imaging system 60 according to another embodiment of the invention. The imaging system 60 includes one or more transceivers 10 in accordance with one or more of the previously disclosed embodiments. The one or more transceivers 10 may be positioned in supporting cradles 50 that are operably coupled to portable computing devices 62, which in turn, are suitably configured to receive imaging data from the one or more transceivers 10 through the communications link 38. The communications link 38 may be a conductive link, as shown in FIG. 6, or it may be a wireless radio frequency link or an optical link, such as a wireless infrared link. The portable computing devices 62 communicate with a server 66 over a communications network 72. Although two transceivers 10 are shown in the networked imaging system 60 shown in FIG. 6, fewer than two, or more than two transceivers 10 may be present. In addition, the processing of ultrasound signals may be divided between the transceiver 10, the portable computing devices 62, and the server 66. For example, the transceiver 10 may be configured to process the ultrasound signals and generate an ultrasound image using algorithms in accordance with other embodiments of the invention, or alternately, the ultrasound image may be generated by the portable computing device 62 or even by the server 66 after receiving ultrasound signals from the transceiver 10. In a particular embodiment of the networked imaging system 60, the imaging algorithms that generate the enhanced ultrasound images reside on the server 66. Each of the portable computing devices 62 accordingly receives signals acquired from the transceivers 10 through the cradles 50 and stores the signals in the portable computing device 62. The computing device 62 subsequently retrieves imaging programs and instructions to perform the additional ultrasound enhancement procedures from the server 66. Thereafter, each personal computing device 62 generates various ultrasound images by processing the ultrasound data, including one-dimensional ultrasound images, two-dimensional images, three-dimensional renderings, and enhanced images from the retrieved imaging programs and instructions. The generated images may be stored on the server 66.

In another particular embodiment, the imaging programs and the instructions reside exclusively on the server 50 and are executed on the server 50. Each portable computing device 62 receives the acquired signals from the transceivers 10 through the cradle 50 and transfers the acquired signals to the portable computing device 62. The device 62 subsequently communicates the signals to the server 66 and processes the signals to generate the desired ultrasound images, including one-dimensional images, two-dimensional images, three-dimensional renderings, and other similar images. The ultrasound images may be stored on the server 66, or alternately, the images may be transferred to one or more of the personal computing devices 62.

Figure 7:
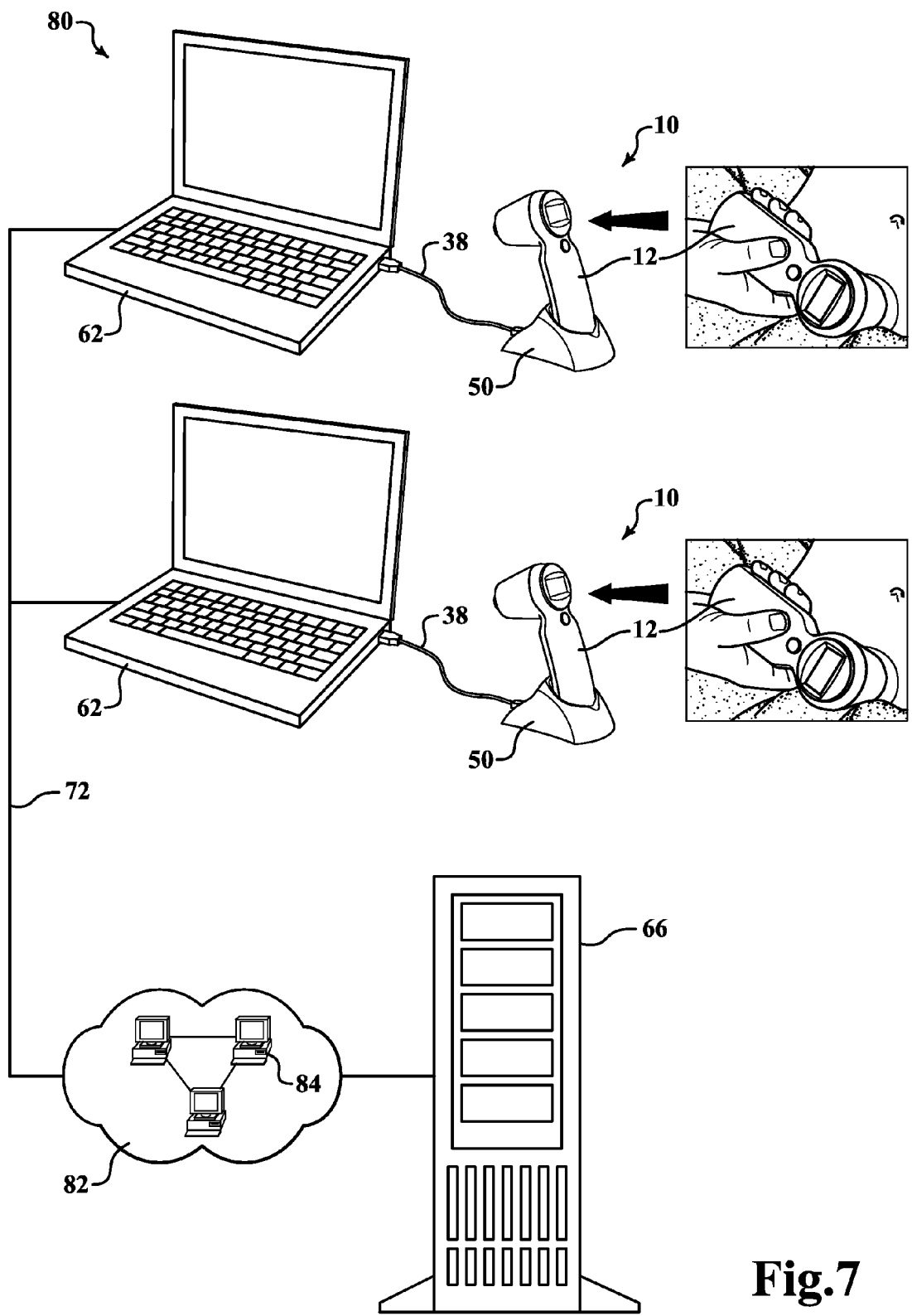
FIG. 7 is a schematic view of a plurality of bladder wall measuring systems connected to a server over the Internet or other network.

FIG. 7 is a partial isometric and diagrammatic view of a networked imaging system 80 according to still another embodiment of the invention. Many of the elements of the present embodiment have been discussed in detail in connection with other embodiments, and in the interest of brevity, will not be discussed further. The networked imaging system 80 includes a public data network 82 interposed between the communications network 72 and the server 66. The public data network 82 may include a LAN, a WAN, or the Internet. Accordingly, other computational devices 84 associated with the public data network 82 may communicate imaging data and/or ultrasound images with the portable computing devices 62 and the server 66. Although two transceivers 10 are shown in the networked imaging system 80 shown in FIG. 7, fewer than two, or more than two transceivers 10 may be present.

Figure 8:
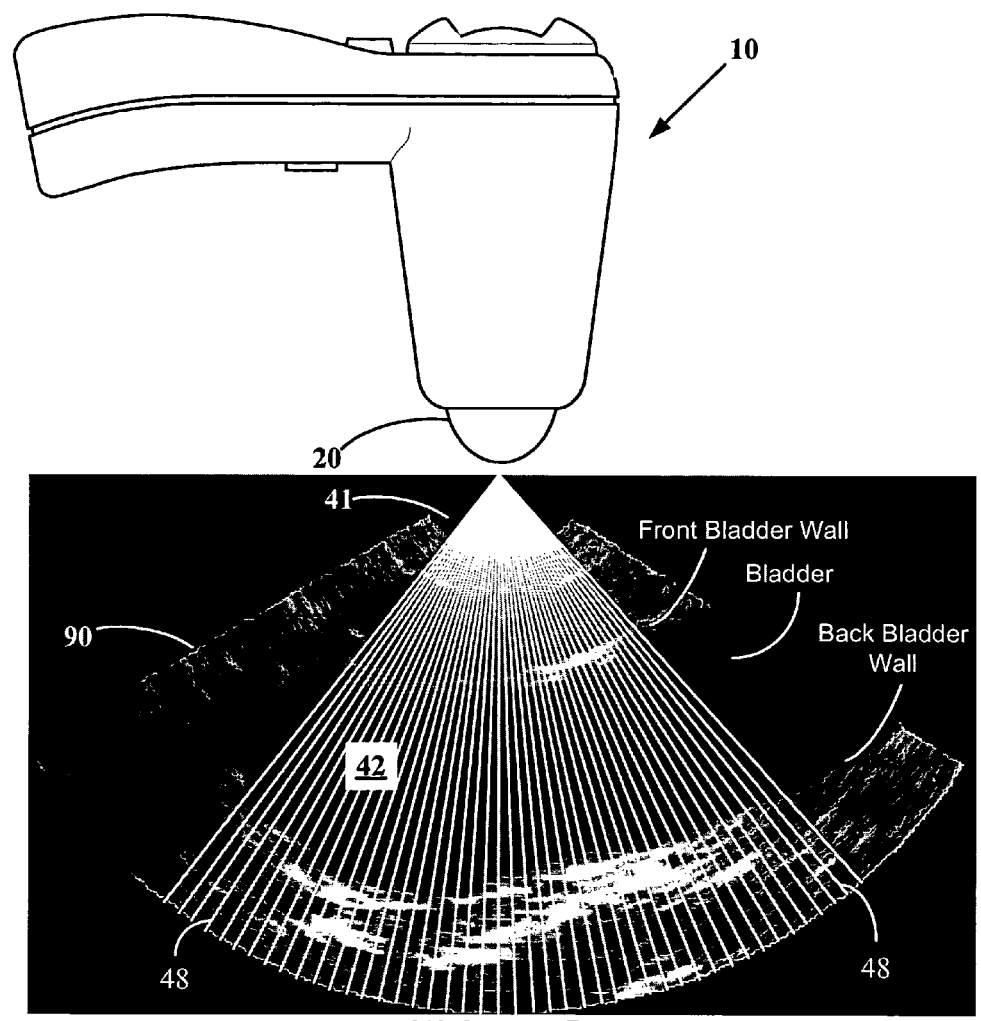
FIG. 8 illustrates a scan plane image with diagrammatic scan lines overlaid on the image.

FIG. 8 is an ultrasound image 90 of a bodily portion of a patient that will be used to describe other embodiments of the invention. The image 90 is formed by projecting a plurality of scan lines 48 downwardly into a selected anatomical portion of the patient to form the fan-like scan plane 42. The scan plane 42 may be rotated about an axis that extends through the transceiver 10 to generate a scan cone 40 (as shown in FIG. 3A) to obtain three-dimensional imaging information for the selected anatomical portion. Accordingly, when ultrasound energy is projected into the selected anatomical portion, various internal structures may reflect the ultrasound energy, including a bladder, a front bladder wall and a back bladder wall. The bladder may contain a volume of a fluid, such as urine, as shown in FIG. 8. The foregoing structures typically present imaging resolution difficulties. In particular, an ultrasound image may fail to adequately resolve a fluid-filled cavity, or a tissue that forms a boundary of the fluid-filled cavity, or still other structural details present in the imaged anatomical portion. Moreover, the foregoing structures generally respond to ultrasound energy in a non-linear manner, so that reflected ultrasound echoes include one or more harmonics of a fundamental ultrasound frequency.

One measure of the non-linear behavior of various fluids and tissues is the Goldberg number (G). G is a dimensionless quantity that generally relates ultrasound attenuation to harmonic distortion due to non-linear effects in a tissue or a fluid when subjected to ultrasound energy. Accordingly, when G is about one, non-linear effects are comparable to attenuation effects in the tissue. When G is much greater than one, such as for water or urine, the nonlinear processes are dominant. When G is less than one, as in soft tissue, attenuation effects are more dominant. For example, it is known that fatty tissue has a Goldberg number of approximately about 0.27, while blood, liver, and muscle have a G value of approximately about one. In contrast, fluids such as urine have a G value of approximately about 104.

Figure 9:
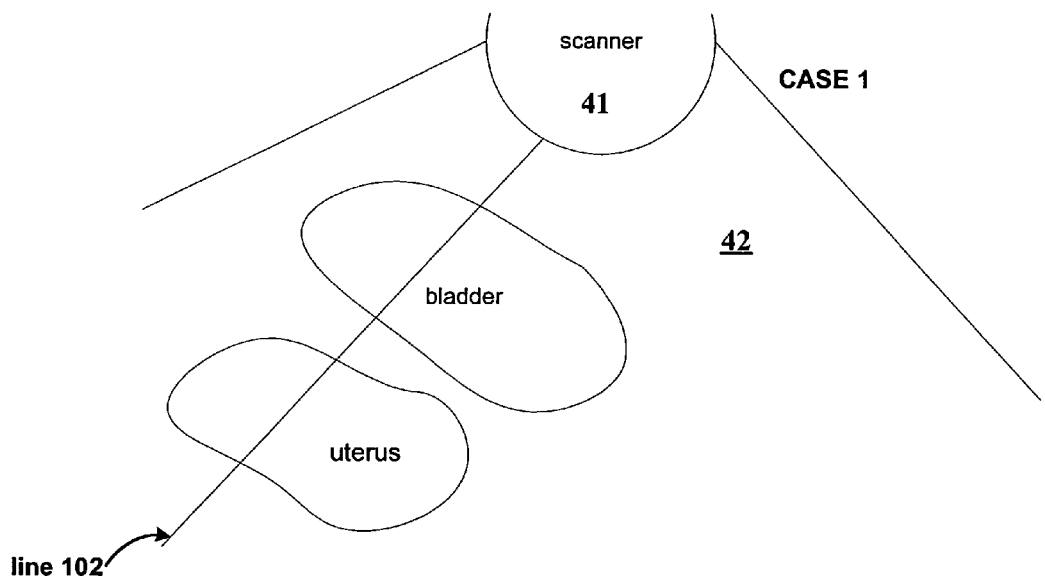
FIG. 9 is a schematic illustration of a scan line passing through a full bladder and a uterus.

With reference now also to FIG. 9, the scan plane 42 may include at least one scan line 102 that extends through a bladder and a uterus of a female patient. In this condition, referred to as a "case 1" condition in FIG. 9; the bladder includes a relatively large volume of urine. Typically, the bladder and the uterus appear as low echogenicity regions when the anatomical region shown in FIG. 9 is scanned. Known image processing software (incorporated herein by reference from one or more of the references listed in the priority claim section) may be used to image the shallowest region of low echogenicity. Since the low echogenicity region is generally preferentially selected, so that no imaging ambiguity exists, and the bladder is therefore readily identifiable.

Figure 10:
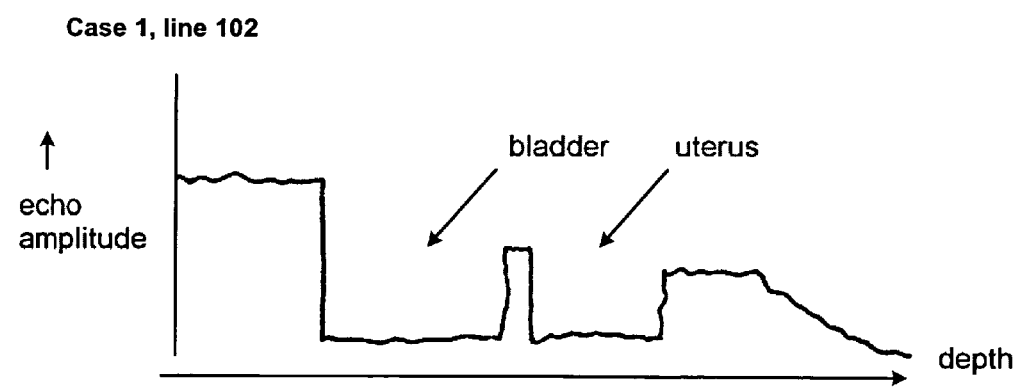
FIG. 10 is a plot of echo amplitude versus scan line depth of the FIG. 9 schematic.

Referring now to FIG. 10, a typical echo amplitude response for the anatomical region of FIG. 9 is shown. The echo amplitude response as depicted in FIG. 10 may be obtained through application of one or more of the algorithms incorporated by reference herein. For example, the computational algorithms disclosed in U.S. Pat. No. 6,676,605 to Barnard et al, U.S. Pat. No. 5,235,985 to McMorrow et al, and U.S. Pat. No. 4,926,871 to Ganguly et al, may be used.

When both organs are relatively filled with a fluid (as shown in FIG. 9), the edges of the bladder and uterus are relatively detectable and are thus generally distinguishable. In this case, the relatively full bladder presents a relatively U-shaped valley at a shallower bodily depth. In contrast, a corresponding U-shaped plateau presented by the uterus is generally identifiable at a greater bodily depth. Thus, while the embodiments of the present invention can improve accuracy and diagnosis in the foregoing situation where both organs are relatively filled with a bodily fluid, the embodiments are also suited to imaging bodily regions when one or both of the organs is less than full.

Figure 11:
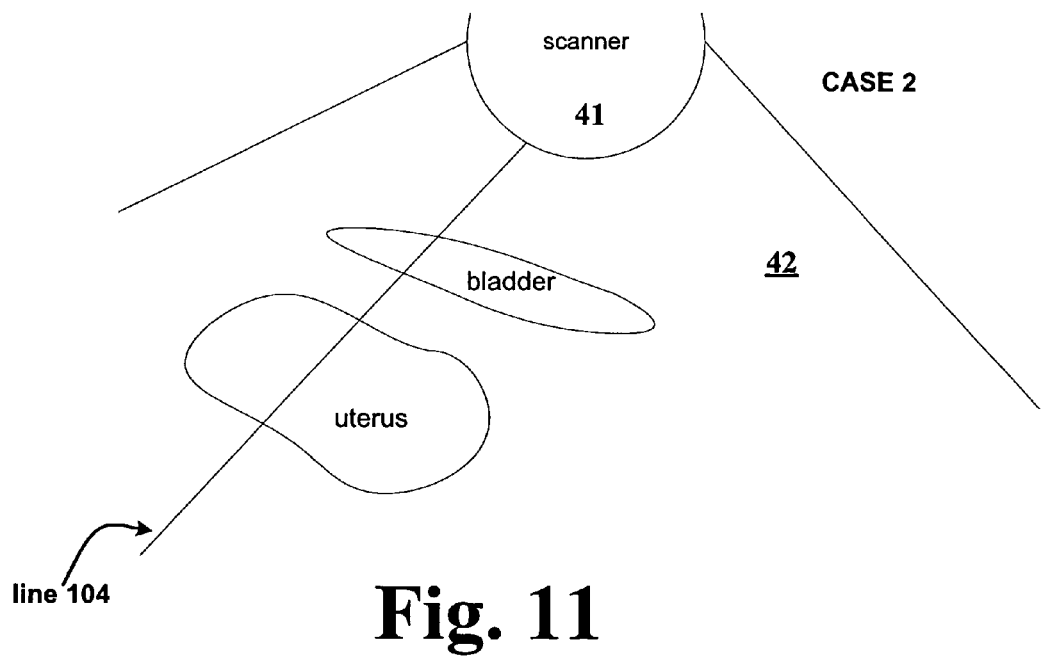
FIG. 11 is a schematic illustration of a scan line passing through a near empty bladder and the uterus.
Figure 12:
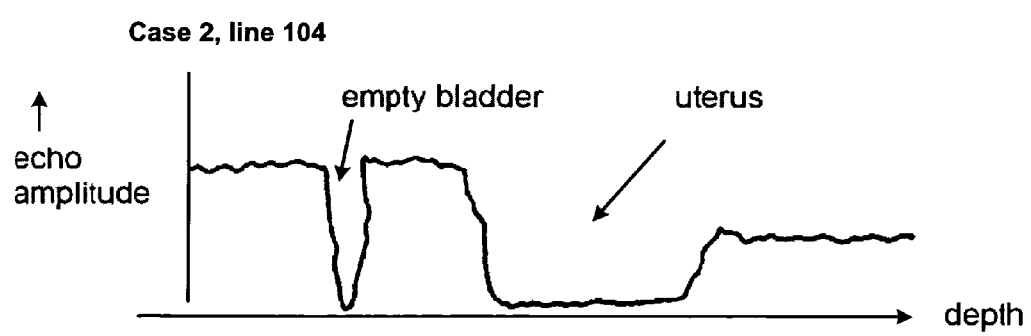
FIG. 12 is a plot of echo amplitude versus scan line depth of the FIG. 11 schematic.

FIG. 11 is a diagrammatic representation of the anatomical region of FIG. 9, wherein the at least one scan line 104 extends through the bladder and the uterus when the bladder contains a relatively low volume of urine. This condition is referred to as "case 2" in FIG. 11. Because the bladder volume is greatly reduced in the Case 2 situation in comparison to the Case 1 condition shown in FIG. 9, the low echogenicity region is now principally located in the uterus. In current image processing methods, an average of the low echogenicity regions is compared to a threshold value to distinguish between the bladder and the uterus, which may tend to contribute to imaging errors. FIG. 12 is an echo amplitude response corresponding to the anatomical region of FIG. 11. The relatively empty bladder presents a relatively narrow valley. In contrast, the uterus generates a relatively wider U-shaped valley. As a consequence, the bladder is less readily distinguishable from the uterus when the bladder contains a low volume of urine. The disclosed embodiments better address the foregoing problems by using algorithms that more accurately detect ultrasound signal harmonic differences between cavity-residing fluids adjacent to enclosing tissue interfaces.

Figure 13:
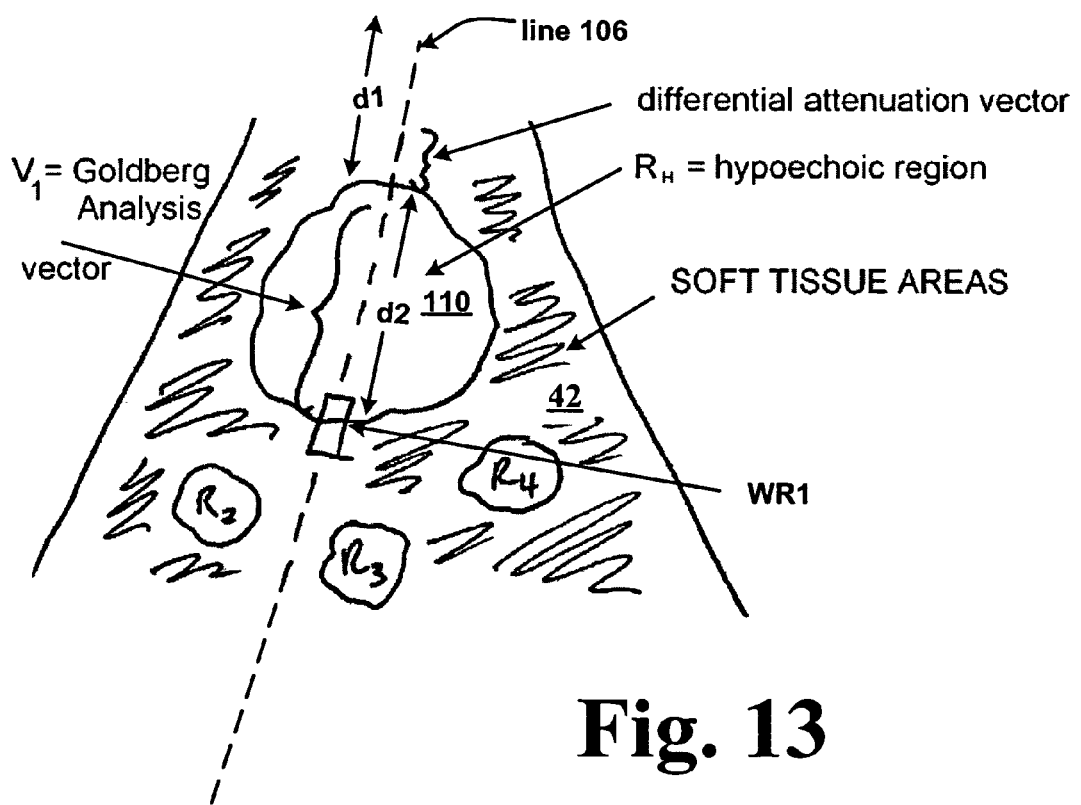
FIG. 13 is a schematic illustration of a scan line passing through body cavities and surrounding tissues.

FIG. 13 is a diagrammatic representation that will be used to illustrate a method for imaging an anatomical region according to an embodiment of the invention. An A-mode scan line 106 is projected into a first bodily cavity 110, for example, a bladder and a uterus as depicted in FIGS. 9 and 11 for the respective case 1 (which corresponds to a relatively full bladder) and case 2 (which corresponds to a nearly empty bladder). The projected ultrasonic waveform is altered by the tissue along the distance $d_1$ of the scan line 106, which corresponds to tissue preceding the cavity 110, and by the distance $d_2$ that corresponds to an interior portion of the cavity 110 along the scan line 106. Other intervening cavities along the scan line 106, such as a uterus, may also alter the projected ultrasound waveform.

The first cavity 110 is hypoechoic and designated as region $R_H$. Other differentially echoic regions illustrated in the scan plane 42 include hypoechoic regions $R_3$, $R_4$, and $R_5$. Ultrasound energy passing through and within the body cavities 110 along scan line 106 may be subjected to an image analysis algorithm to determine respective volumes of each cavity, namely $V_1$ corresponding to the cavity 110. Signals reflected from the back wall or other boundaries of the first body cavity 110 are window function processed in a window region designated as WR1. The WR1 region spans a portion of the tissue adjacent and distal to the cavity 110 backwall interface and further spans a portion of the cavity space along the scan line 106 proximate to the cavity 110-backwall interfaces.

In the WR1 region, window function processing determines the raw data comprising the fundamental frequency $f_o$ and a selected higher order harmonic $2f_o$ that is generated within the WR1 space along the scan line 106. The magnitude of the higher order harmonic generated within WR1 varies because different tissues and/or fluids are encountered by the scan line 106 as it projects into the body. Consequently, a fluid volume and a fluid composition within the cavity 110 alters the magnitude of the higher order harmonic $2f_o$ near the scan line 106 that is proximate to the back wall interface of the cavity 110.

Figure 14:
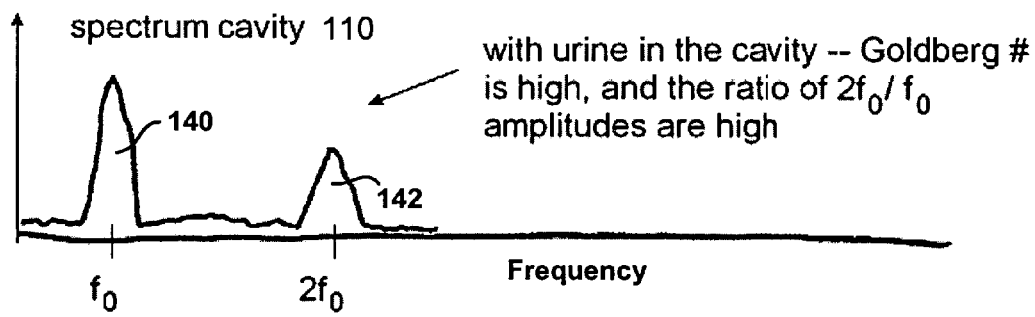
FIG. 14 is another spectral plot of a window function processed insonified region of FIG. 13 for a non-pregnant female subject having homogeneous uterine fluid.

FIG. 14 is a spectral plot of the insonified region of FIG. 13 that corresponds to a non-pregnant female with a uterus and nearly full bladder. The fundamental frequency $f_0$ has a peak value 140 and the higher order harmonic $2f_0$ has a peak value 142. The fundamental and harmonic peaks 140 and 142 are a result of window function processing the corresponding echo amplitude response. The magnitude of the harmonic peak 142 may be normalized by dividing the peak 142 by the fundamental frequency peak 140. Accordingly, it is noted that a high Goldberg number stemming from urine in the nearly full bladder corresponds to a high magnitude for the frequency ratio. Different urine volumes and/or the presence of other organs, such as a uterus may also alter the magnitude of the frequency ratio. The magnitude of the second harmonic peak 142 in the first cavity 110 is affected by the presence of the uterus and the urine volume and urine composition contained within the bladder. The composition and volume of the urine may thus be determined.

Figure 15:
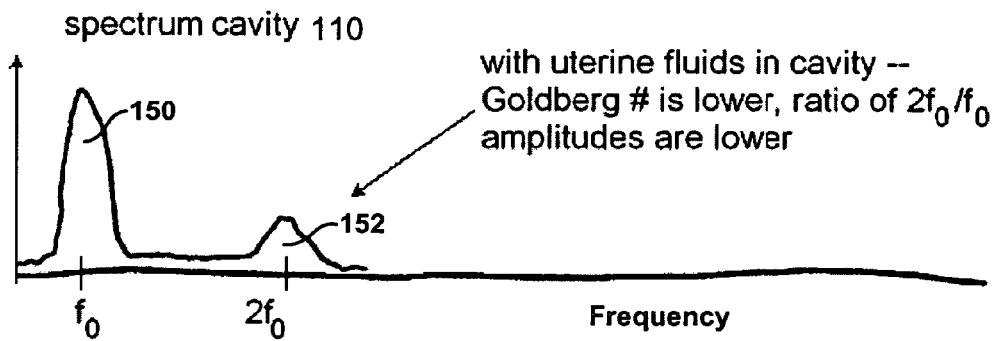
FIG. 15 is another spectral plot of a window function processed insonified region of FIG. 13 for a non-pregnant female subject having heterogeneous uterine fluid.

FIG. 15 is a spectral plot of the insonified region of FIG. 13 in a non-pregnant female with a uterus and nearly empty bladder and having greater amounts of blood and tissue containing uterine fluid. The spectral plot is within the window region WR1 and shows the fundamental peak 150 and the higher order harmonic peak 152 resulting from frequency domain processing of the corresponding echo response. As shown, the harmonic spectrum within WR1 of the non-pregnant female exhibits a generally lower Goldberg number than a non-pregnant female with a substantially greater fluid volume. The magnitude of the frequency ratio $(2f_0/f_0)$ is correspondingly lower. Urine fluids mixed with blood at variable compositions may also alter the magnitude of the higher order harmonic peak 152 shown in FIG. 15. Accordingly, the reflected spectral components generated within the first cavity 110 may have a still lower harmonic ratio $(2f_0/f_0)$ as compared to unmixed uterine fluids depicted in FIG. 14, since the mixed fluid mixtures generally exhibit a lower Goldberg number.

With reference still to FIGS. 14 and 15, an embodiment of the invention will now be described. The present embodiment is based on non-linear wave propagation and variations in the attenuation of ultrasound energy in body fluids. The back wall ultrasound spectrum is processed to determine a reflected harmonic content, and this harmonic content is compared to the content of the fundamental ultrasound energy by forming the frequency ratio. The resulting value may then be adjusted for differences in attenuation at a selected frequency j between $f_0$ and $2f_0$ in the intervening tissue i, as described below.

For a selected window, the total attenuation of the fundamental frequency component may be expressed as follows in equation E1:

$$A_{f_0} = 2d_1\sigma_{11} + 2d_2\sigma_{21} \approx 2d_1\sigma_{11} \text{ dB} \quad \quad \quad E1$$

where: $\sigma_{ij}$=attenuation coefficient of a tissue i at a frequency j and distances $d_1$ and $d_2$ are as shown in FIG. 13.

While the total attenuation of the higher order harmonic frequency component may be expressed as follows in equation E2:

$$A_{2f_0} = 2d_1\sigma_{12} + 2d_2\sigma_{22} \approx 2d_1\sigma_{12} \text{ dB} \quad \quad \quad E2$$

A difference in the attenuation of higher order harmonic component to the fundamental component is therefore defined by equation E3:

$$A_{ratio} = 2d_1(\sigma_{21} - \sigma_{11}) \text{ dB}. \quad \quad \quad E3$$

For example, in soft tissue having an attenuation factor of about 1.1 dB/cm, the attenuation coefficient $\sigma_{12}$ is approximately about 3.7 dB/cm, when $f_0$=3.7 MHz. Accordingly, the amplitude ratio becomes in equation E4:

$$A_{ratio} = 2d_1(3.7 \text{ dB/cm}) \quad \quad \quad E4$$

Based upon the foregoing, harmonic power amplitudes and frequency ratios may be derived and associated with known fluid volumes and fluid compositions derived from living subjects and/or non-living experimental devices, which are then encoded into readily accessible look-up tables, calibration plots or other suitable means for encoding data having utility in measuring the fluid volumes or identifying fluid compositions in an insonified subject.

Figure 16:
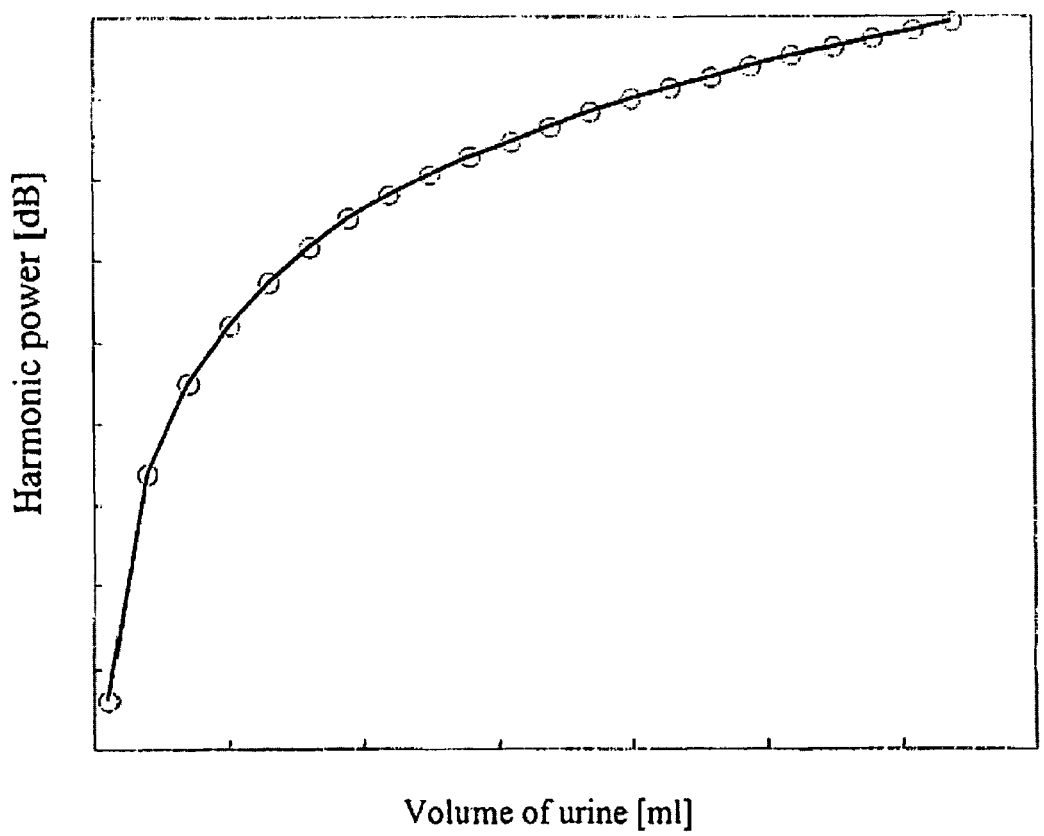
FIG. 16 is a calibration plot of harmonic power as a function of the bladder volume.

FIG. 16 is an example of a calibration plot of harmonic power as a function of the bladder volume in a subject. The harmonic power may be obtained from a look-up table that includes data corresponding to different bodily tissues and fluids. The calibration plot thus permits the determination of a urine volume when the higher order amplitude and the fundamental frequency amplitudes are expressed as the ratio $2f_0/f_0$. Alternate embodiments may include calibration plots for other fluid compositions that stem from data in respective look-up tables that are enhanced by the foregoing window functions. For example, a mixture of amniotic fluid and blood, or amniotic fluid/blood/urine mixtures would have a particular calibration plot. The plot shown in FIG. 16 may alternately be expressed using a suitable curve fitting procedure, such as, for example, a linear least squares procedure, a spline procedure, a polynomial procedure or other known curve fitting procedures.

In still another particular embodiment, the Goldberg number may be used to distinguish between a urinary bladder and a uterus in post-void scans in a female subject. Because the uterus generally appears as a dark structure in ultrasound images, it may be erroneously identified as the urinary bladder in post-void scans. To avoid this, the present embodiment provides that the harmonic amplitudes are calculated on a post-void scan of a female bladder. If a selected combination of harmonic amplitudes is higher than a selected threshold value, the scan likely contains a fluid. Otherwise, the scan likely contains the uterus of the female subject.

In still yet another particular embodiment, the harmonic amplitudes may be calculated based upon one or more selected ultrasound lines, or upon all of the ultrasound lines within the total image. In addition, the harmonics may be calculated within a region-of-interest or lines-of-interest when guided by features detected on the B-mode image, such as a region behind a posterior wall of a fluid-filled cavity.

In still another particular embodiment, inter-patient variability in the harmonic amplitudes may be normalized or otherwise adjusted using a combination of transmission features, such as, for example, frequency, peak-to-peak voltage, pulse length, and other transmission features. Other features may be extracted from B-mode images, such as a depth of an anterior wall of a fluid-filled cavity.

Figure 17:
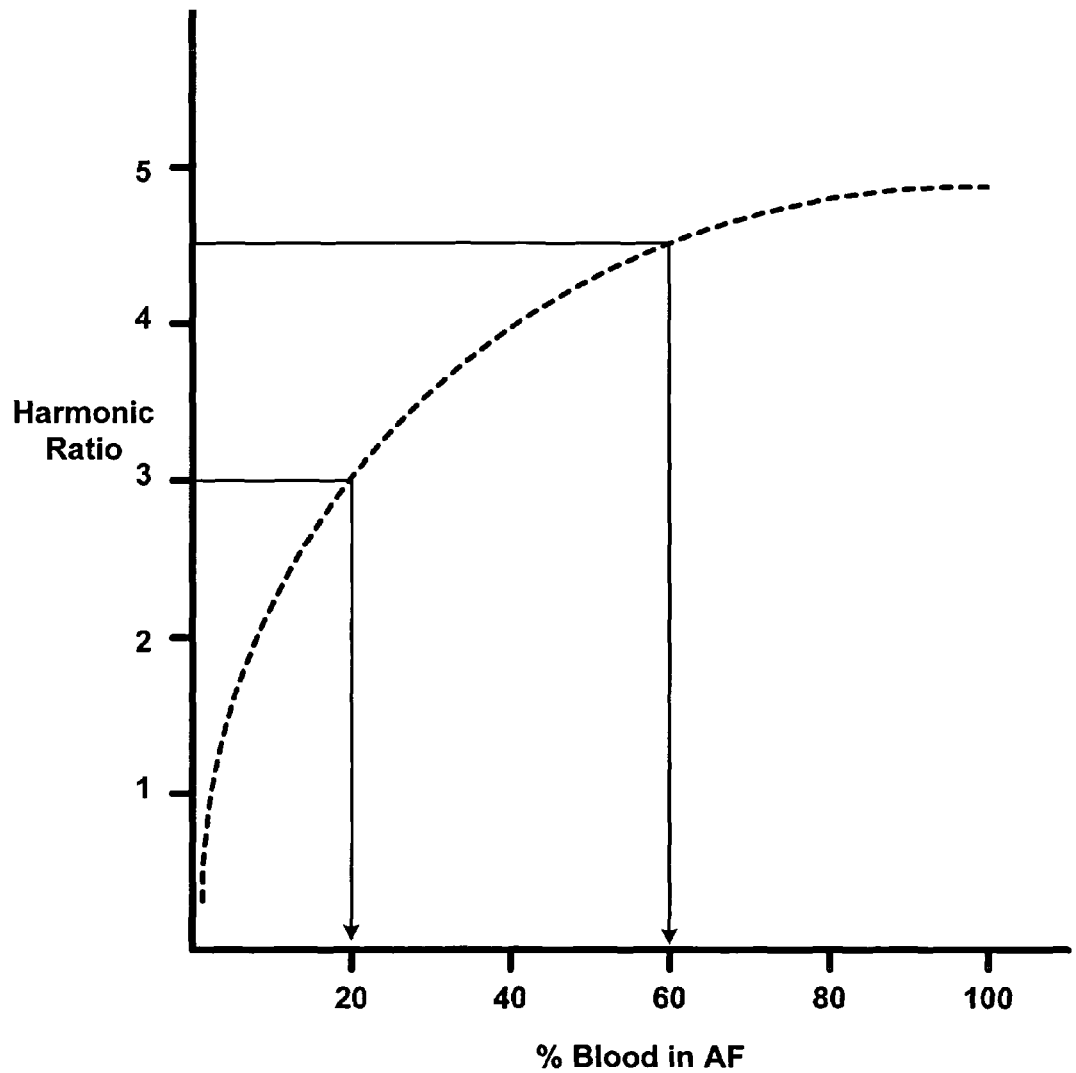
FIG. 17 is a calibration plot of harmonic ratio as a function of blood composition in amniotic fluid.

FIG. 17 is a calibration plot of a harmonic ratio expressed as a function of a blood composition in the amniotic fluid. A dashed calibration line may be used to graphically determine a blood percentage composition. The Goldberg number may also be used to differentiate between various bodily fluid compositions, such as, for example, a transudate and an exudate fluid developed in a lung of a subject, or in compositions of urine. It may also be used to detect the presence of blood within a bodily fluid, such as in amniotic fluid, or in urine. The harmonic ratio differences between the fluids may thus be used to identify a composition of a fluid. For example, as shown in FIG. 17, a harmonic ratio of 3 corresponds to an amniotic fluid having a blood composition of approximately 20%. Similarly, a harmonic ratio near 4.5 corresponds to an amniotic fluid having approximately 60% blood composition.

In still yet another particular embodiment, the Goldberg number may also be used to distinguish between blood and amniotic fluid in the uterus of a pregnant female. Because blood has a significantly lower Goldberg number compared to amniotic fluid, the second harmonic distortion resulting from a region containing blood is different from a region containing amniotic fluid. The Goldberg number and the harmonic ratio may thus be utilized to differentiate between blood and amniotic fluid and to confirm an identification of the fluid that is isonofied. For example, certain pregnant subjects having a low amniotic fluid volume. Accordingly, the uterus becomes more engorged with blood, making identification of the amniotic fluid regions more difficult. To address this problem, the embodiments of the present invention utilize the Goldberg number and harmonic ratio to assist in the identification process. In a further example, blood appears very dark and similar in appearance to amniotic fluid in a B-mode image. Thus, while measuring an amniotic fluid volume in B-mode images, blood may be detected in the umbilical cord or in the vessels in walls of the uterus and erroneously identified as amniotic fluid. Using the second harmonic distortion in conjunction with the Goldberg Number assists in discriminating between amniotic fluid and blood.

In still another particular embodiment, the Goldberg number may also be used to identify, classify, and measure a volume of a fluid in the lungs for pleural effusion.

In another embodiment, an ultrasound image may be created that shows selected combinations of harmonic amplitudes throughout the ultrasound image that permits detection of various fluid regions that would typically be indicated by presence of higher harmonics. The selected combination of the harmonic reflections may be embodied in a software program, or alternately as an improvement to an existing software program in conventional harmonic imaging ultrasound equipment. The harmonic ratio may then be normalized by the factor, $A_{ratio}$. The results may then be compared to an empirically derived look up table or calibration plot that describes one of the attenuation or harmonic characteristics for each kind of tissue (see FIG. 16). Accordingly, tissues and bodily fluids with low Goldberg numbers and low harmonic ratios can thus be differentiated from tissue and body fluids with higher Goldberg numbers and higher harmonic ratios. The use of the foregoing harmonic ratios and look-up tables (or equivalent calibration plots) in the manner described provides another basis to further differentiate and enhance a display of fluid and tissue regions. For example, a low volume to near empty bladder may be suitably differentiated from a uterine cavity and adjacent tissue.

In another embodiment of the invention, an additional adjustment may be performed to compensate for a "shock formation distance" that may occur along a given scan line. Shock formation distances relate to Goldberg numbers as a consequence of an energy transfer that occurs in the tissues and nearby fluids as the fundamental ultrasound frequency is transformed to a harmonic frequency. For example, an excitation frequency of 3.7 MHz results in significant harmonic generation in human tissue. Thus, the distance $d_2$ (FIG. 13) may also be used to adjust the harmonic amplitude ratio.

Figure 18:
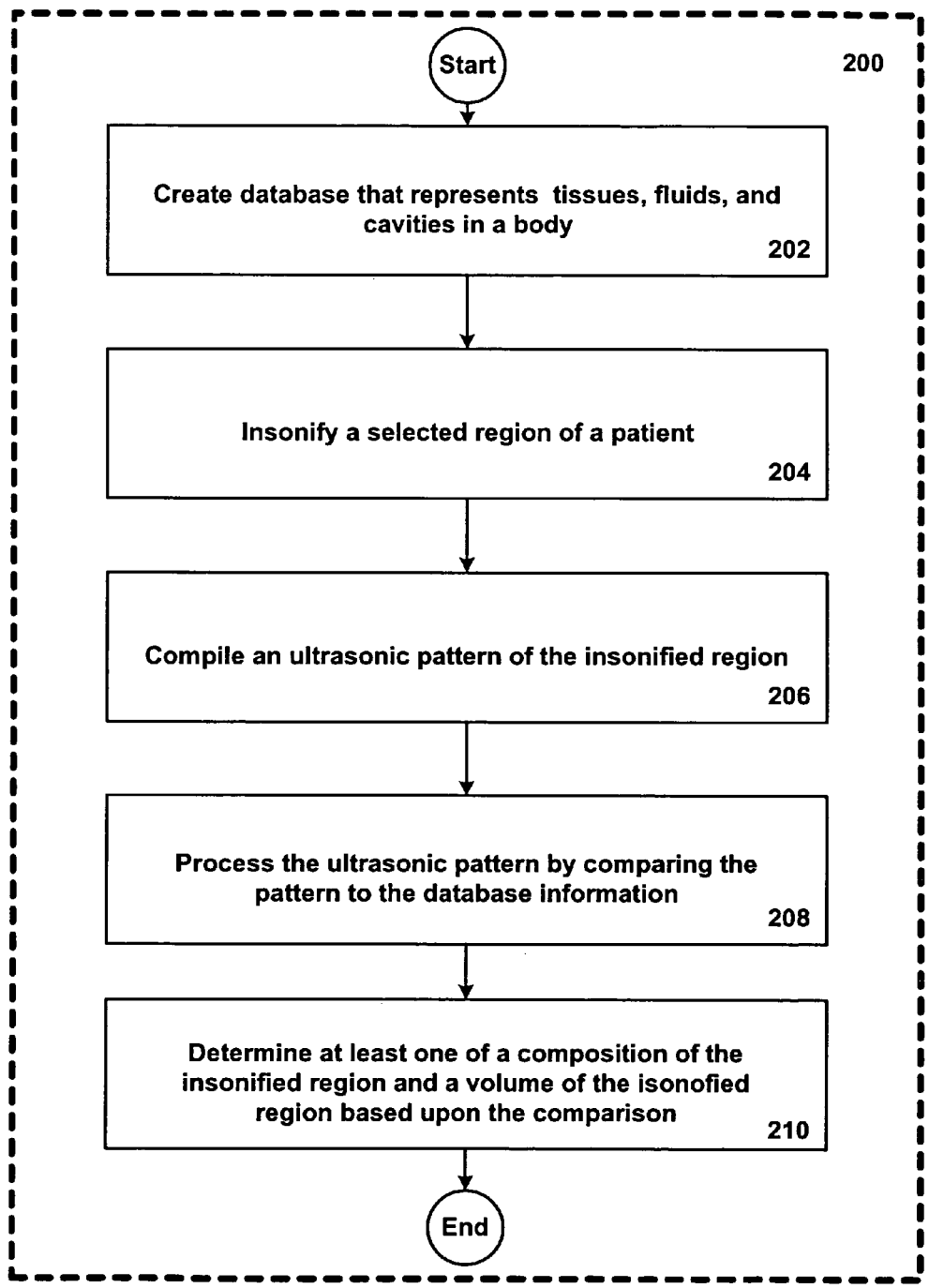
FIG. 18 is a method overview flowchart.

FIG. 18 illustrates a flow chart of a method 200 of measuring fluid volumes and classifying fluid compositions, according to an embodiment of the invention. The method 200 begins by creating a database that includes attenuation and/or harmonic characteristics of tissues, fluids, and cavities of a body at block 202. The database may be further characterized by sex, age, morphological, physiological, and pathological states. The method 200 continues by isonifying a selected region of a patient at block 204. Thereafter, ultrasonic patterns of the insonified region of the patient are compiled at block 206 (see FIG. 19 below). The method 200 continues by processing the ultrasonic patterns and comparing the processed patterns to the database information at block 208. For example, the processed patterns may be compared using the volume calibration plot of FIG. 16 and the composition calibration plot of FIG. 17. Thereafter, the method 200 concludes by determining at least one of a composition of the insonified region and a volume of the insonified region based upon the comparison of the patient's ultrasonic patterns to the database's content at block 210. Ultrasonic measurement data obtained from the subject at block 210 may then be applied to a volume calibration plot similar to FIG. 16 to obtain volume measurements. Similarly, ultrasonic measurement data obtained from the subject at block 210 can be applied to a composition calibration plot similar to FIG. 17 to obtain fluid composition measurements.

Still referring to FIG. 18, the processed patterns from the subject may be compared to the look-up table or calibration plot as depicted in FIG. 16 to obtain volume information. To obtain a compositional determination or classification of a given detected fluid, in accord with FIG. 17, the type of bodily fluids contained within a cavity may be ascertained through a comparative analysis of the Goldberg numbers, harmonic ratios, and attenuation factors within the insonified region. The Goldberg numbers; harmonic ratios, and attenuation factors stored within a database may then be accessed to determine the fluid composition. A fluid composition may thus be determined by accessing a calibration plot, interpolating from a look-up table, or applying regression analysis, as previously described. The volume and compositional look up tables or calibration plots illustrated in FIGS. 16 and 17 may be obtained from ultrasound information databases derived from simulated human models, accumulating clinical measurements obtained from patients stored in a separate database, or a combination of simulated models and clinical measurements. Other databases may include simulated animal models with or without a veterinary-based database. Yet other databases may include a combination of human and veterinary sourced databases.

Similarly, tissue types or combinations thereof within the insonified region are determined by comparative analysis between the Goldberg numbers, harmonic ratios, and attenuation factors presented by the insonified region of the patient to those same numbers, ratios, and factors stored in the database.

Figure 19:
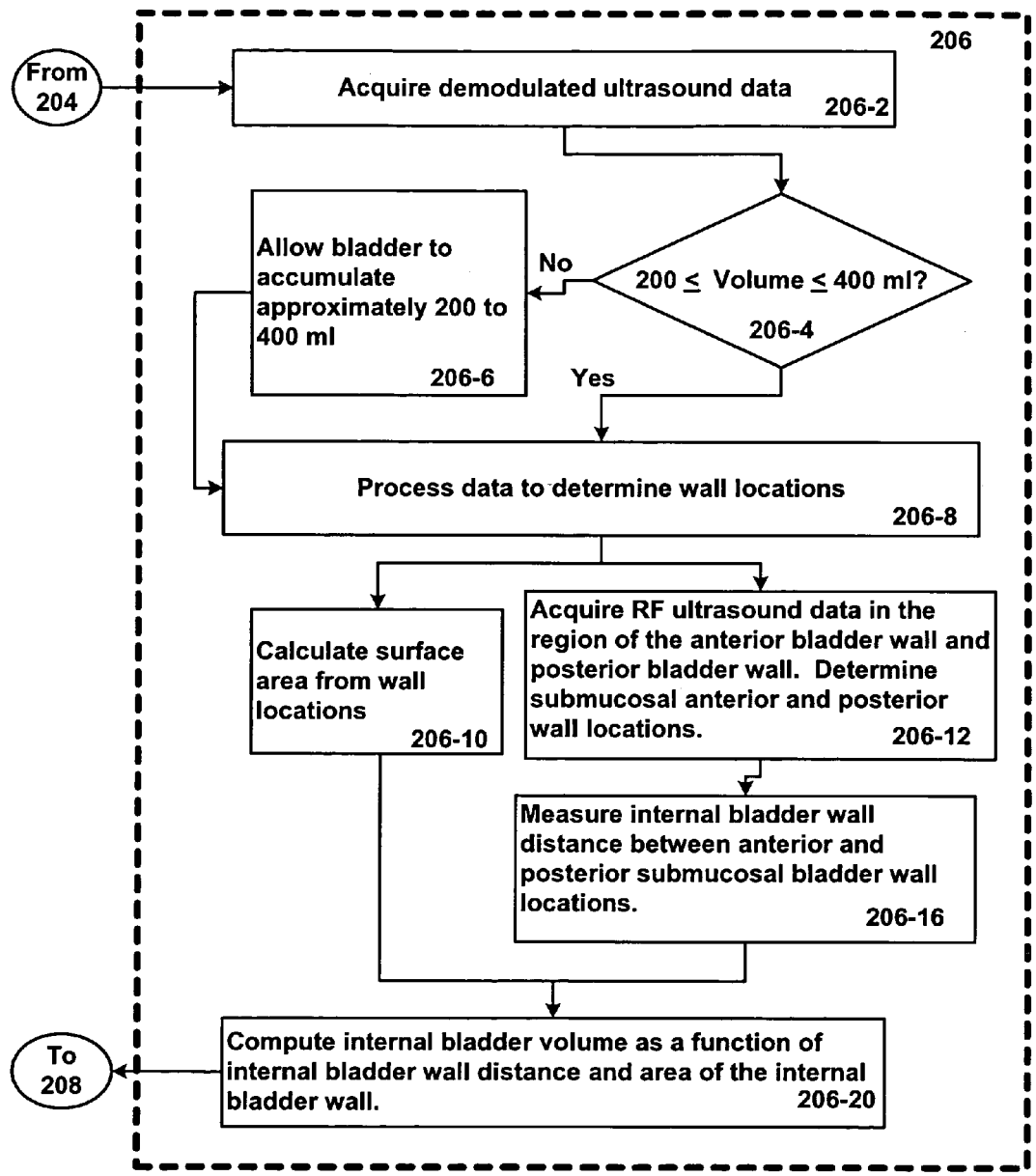
FIG. 19 is an expansion of sub-algorithm 206 of FIG. 18.

FIG. 19 is an expansion of sub-algorithm 206 of FIG. 18. Sub-algorithm 206 permits the determination of volume of an organ wall, the mass of an organ wall, the internal organ volume defined by an inner perimeter of an organ wall, and the outer organ volume defined by the outer perimeter of an organ wall from echogenic patterns received from an insonified region. The ultrasonic patterns of the insonified region having at least one organ of the patient are compiled at process block 206-2. Once the wall locations are identified, the wall locations, demodulated magnitude data, and a subset of quadrature amplitude demodulated signals in the region of the anterior bladder wall are directed to the microprocessor for further analysis according to the algorithm illustrated in FIG. 19 for the particular embodiments. First, ultrasound data is acquired relative to the bladder, uterus, or other organs as shown in the first block 206-2. In general, bladder-specific data can be acquired by a user who manipulates the transceiver 10 while viewing the received data on a display screen and then positioning the transceiver 10 as necessary so that an organ or organs, such as a bladder and uterus, are sufficiently within the field of view of the cone as depicted in FIGS. 2 and 3A.

Referring again to FIG. 19, and limiting the discussion to a specific organ, for example a bladder, echogenic data is collected by the transceiver 10. After obtaining ultrasound bladder data, the ultrasound data is processed to determine if the bladder contains approximately 200 to approximately 400 ml, as shown in the second process block 206-4 represented as a decision diamond. If "No" to the query "200 ml≦volume≦400 ml?", then the bladder is allowed to accumulate approximately 200 to approximately 400 ml, as shown in the third process block 206-6, or, if "Yes", meaning the bladder already contains the preferred approximate 200-400 ml volume, then the locations of the bladder walls, as shown in the fourth block 206-8, may be undertaken. The determination of organ wall locations and other such exterior boundaries within an ultrasound scan are within the capability of ultrasound devices presently on the market. In general, however, the process determines the length of a scan line from the transceiver dome to the bladder wall. The data, including wall locations, is stored in the memory of the computer 62 and is used to determine whether or not the bladder volume is within a range of approximately 200 to approximately 400 ml. If the bladder volume is within that range, the ultrasound data is used to determine the actual surface area from the wall locations, as indicated in the fifth block 206-10. The application of previously described methods using harmonic ratios, powers, and Goldberg G-numbers may be used to enhance the accuracy of thickness, area, volume, and mass determinations of bladders holding fluids within the approximate 200-400 ml range. The surface area calculation is explained with regard to FIG. 21 below and allows for calculation of an outer bladder wall surface area defined by subserosal locations 372A and 372B and an inner bladder wall surface area defined by submucosal locations 374A and 374B. While calculating the surface area in the fifth block 206-10, reflected ultrasound waves are received from the anterior bladder wall, as indicated in the sixth block 206-12. Although these tasks are preferably conducted in parallel, they may alternatively be processed in series. Thereafter, as shown in the seventh block 206-16, the bladder wall thickness is determined from the coherent signals that overlap at the wall locations. The determination of bladder wall thickness is explained in greater detail below. Finally, as shown in the seventh block 206-16, the bladder wall distance is computed as a difference between panterior and posterior submucosal bladder wall locations. Thereafter, at the eighth process block 206-20, the internal bladder volume is computed as a function of the internal bladder wall distances and the area of the internal bladder wall.

The volume restriction indicated in the previous paragraph is included as the range of bladder volumes that allow for an optimal measurement of the bladder wall mass, bladder wall volume, and internal bladder volumes. The volume and mass calculations may be performed at a volume not in this range, but will result in a less accurate measurement that can be corrected by application of the foregoing described methods using harmonic ratios, powers, and Goldberg G-numbers. For example, bladders having less than 200 ml or that are near empty, the foregoing described methods using harmonic ratios, powers, and Goldberg G-numbers will improve the accuracy of determining bladder wall thicknesses, volumes and mass, and internal and outer bladder volumes. For bladders having fluid volumes substantially greater than 400 ml, for example bladder volumes of 1000 ml to multi-liters, the invention will utilize scan lines greater than 20 cm to accommodate the larger bladder sizes. The invention may be applied to measure the thicknesses, masses, and volumes of internal organs of human and animals. The length of the scan lines is adjusted to match the dimension of the internal organ scanned.

The surface area measurement of fifth block 206-4 is performed by integrating the area of interpolating surface patch functions defined by the wall locations. The mathematical calculations are provided below in greater detail.

The surface of the bladder is defined to be S. This surface corresponds to the actual surface of the bladder determined by analysis of the wall locations of the bladder. Since this shape is not known in advance, modeling the bladder as a sphere or an ellipsoid provides only a crude approximation of the surface. Instead, the surface S is defined as a construction of a series of individual surface patches $s_{ij}$, where i and j count through the latitude and longitude components of the surface, similar to the division of the Earth's surface into lines of latitude and longitude. The area of the bladder surface, S, is defined as the sum of all the individual surface patches, so that $S = \Sigma s_{i,j}$.

Figure 20:
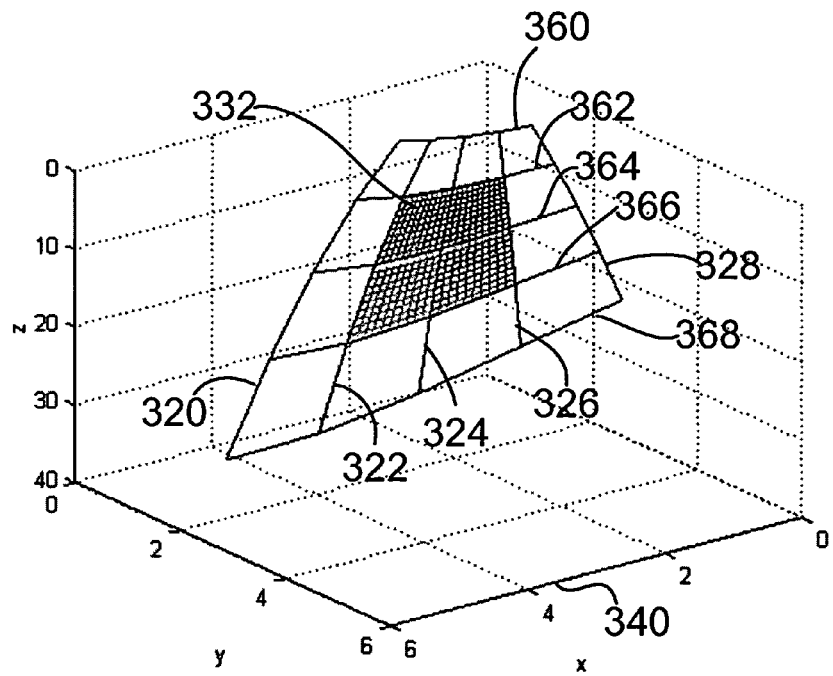
FIG. 20 is a schematic representation of four surface patch elements.

FIG. 20 is a schematic representation of four surface patch elements. As depicted in three dimensions in FIG. 20, by way of example, five scan planes 320-328 are seen transmitted substantially longitudinally across a subserosal wall location 332 referenced to a tri-axis plotting grid 340. The five scan planes include the first scan plane 320, the second scan plane 322, the third scan plane 324, the fourth scan plane 326, and the fifth scan plane 328. The scan planes are represented in the preceding formulas as subscripted variable j. Substantially normal to the five longitudinal scan planes are five latitudinal integration lines 360-368 that include a first integration line 360, a second integration line 362, a third integration line 364, a fourth integration line 366, and a fifth integration line 368. The integration lines are represented in the preceding formulas as subscripted variable i.

By way of example, four surface patch functions are highlighted in FIG. 20 as the subserosal wall location 372. The i and j subscripts mentioned previously correspond to indices for the lines of latitude and longitude of the bladder surface. For the purposes of this discussion, i will correspond to lines of longitude and j will correspond to lines of latitude although it should be noted the meanings of i and j can be interchanged with a mathematically equivalent result. Using the scan plane and integration line definitions provided in FIG. 20, the four surface patch functions are identified, in the clockwise direction starting in the upper left, as $s_{322,362}$, $s_{324,362}$, $s_{324,364}$, and $s_{322,364}$.

The surface patches are defined as functions of the patch coordinates, $s_{i,j}(u,v)$. The patch coordinates u and v, are defined such that $0 \leq u, v < 1$ where 0 represents the starting latitude or longitude coordinate (the i and j locations), and 1 represents the next latitude or longitude coordinate (the i+1 and j+1 locations). The surface function could also be expressed in Cartesian coordinates where $s_{i,j}(u,v) = x_{i,j}(u,v)i + y_{i,j}(u,v)j + z_{i,j}(u,v)k$ where i, j, k, are unit vectors in the x-, y-, and z-directions respectively. In vector form, the definition of a surface patch function is given in Equation 1. k, are unit vectors in the x-, y-, and z-directions respectively. In vector form, the definition of a surface patch function is given in equation E5.

$$s_{i,j}(u,v) = \begin{bmatrix} x_{i,j}(u,v) \\ y_{i,j}(u,v) \\ z_{i,j}(u,v) \end{bmatrix} \qquad \text{E5}$$

With the definitions of surface patch functions complete, attention can turn to the surface area calculation represented in the fifth block 206-10 of FIG. 20. The surface area of S, A(S), can be defined as the integration of an area element over the surface S, as shown in equation E6.

$$A(S) = \int_S dA \qquad \text{E6}$$

Since S is composed of a number of the patch surface functions, the calculation for the area of the surface S can be rewritten as the sum of the areas of the individual surface patch functions as in equation E7.

$$A(S) = \sum_{i,j} A(s_{i,j}). \qquad \text{E7}$$

Similarly to equation E5 for the entire surface, the area of the surface patch is the integration of an area element over the surface patch, shown in equation E8.

$$A(s_{i,j}) = \int_{s_{i,j}} dA_{i,j} \qquad \text{E8}$$

The integration over the surface patch function can be simplified computationally by transforming the integration over the surface to a double integration over the patch coordinates u and v. The transformation between the surface integration and the patch coordinate integration is shown in equation E9.

$$\int_{S_{i,j}} dA_{i,j} = \int_{u=0}^{1}\int_{v=0}^{1} \left|\frac{\partial s_{i,j}}{\partial u} \times \frac{\partial s_{i,j}}{\partial v}\right| dv\, du \quad\quad E9$$

By substituting Equation 5 into Equation 4, and Equation 4 into Equation 3, the area for the entire surface can be calculated. The result of these substitutions is shown in equation E10.

$$A(S) = \sum_{i,j} \int_u\int_v \left|\frac{\partial s_{i,j}}{\partial u} \times \frac{\partial s_{i,j}}{\partial v}\right| dv\, du \quad\quad E10$$

The surface patch function may be any function that is continuous in its first derivatives. In the embodiment shown, a cubic B-spline interpolating function is used for the interpolating surface patch function although any surface function may be used. This interpolating function is applied to each of the Cartesian coordinate functions shown in equation E5. The interpolating equation for the x-coordinate of the $s_{i,j}$ patch function is given in equation E11.

$$x_{i,j}(u,v) = uM_b X_{i,j} M_b^t v^t$$

where t denotes matrix and vector transpose, $$u = \begin{bmatrix} u^3 \\ u^2 \\ u \\ 1 \end{bmatrix}, v = \begin{bmatrix} v^3 \\ v^2 \\ v \\ 1 \end{bmatrix},$$

$$M_b = \begin{bmatrix} -1 & 3 & -3 & 1 \\ 3 & -6 & 3 & 0 \\ -3 & 0 & 3 & 0 \\ 1 & 4 & 1 & 0 \end{bmatrix}, \text{ and } X_{i,j} = \begin{bmatrix} x_{i-1,j-1} & x_{i-1,j} & x_{i-1,j+1} & x_{i-1,j+2} \\ x_{i,j-1} & x_{i,j} & x_{i,j+1} & x_{i,j+2} \\ x_{i+1,j-1} & x_{i+1,j} & x_{i+1,j+1} & x_{i+1,j+2} \\ x_{i+2,j-1} & x_{i+2,j} & x_{i+2,j+1} & x_{i+2,j+2} \end{bmatrix}$$

Similar calculations are performed for the $y_{i,j}$ and $z_{i,j}$ components of the surface patch function.

Since the interpolating functions for each of the patch functions is a cubic surface, the integration may be performed exactly using a quadrature formula. The formula used in this application is shown in equation E12.

$$A(s_{i,j}) = \sum_{i,j} \frac{1}{4}$$

$$\left(\left|\frac{\partial s_{i,j}}{\partial u} \times \frac{\partial s_{i,j}}{\partial v}\right|_{u=\frac{3-\sqrt{3}}{6},v=\frac{3-\sqrt{3}}{6}} + \left|\frac{\partial s_{i,j}}{\partial u} \times \frac{\partial s_{i,j}}{\partial v}\right|_{u=\frac{3-\sqrt{3}}{6},v=\frac{3+\sqrt{3}}{6}} + \left|\frac{\partial s_{i,j}}{\partial u} \times \frac{\partial s_{i,j}}{\partial v}\right|_{u=\frac{3+\sqrt{3}}{6},v=\frac{3-\sqrt{3}}{6}} + \left|\frac{\partial s_{i,j}}{\partial u} \times \frac{\partial s_{i,j}}{\partial v}\right|_{u=\frac{3+\sqrt{3}}{6},v=\frac{3+\sqrt{3}}{6}}\right)$$

Recalling the fact that $s_{i,j}(u,v)$ is defined as a vector function in Cartesian coordinates (Equation 1), the norm of the cross product of the partial derivatives can be written as follows in equation E13.

$$\left|\frac{\partial s_{i,j}}{\partial u} \times \frac{\partial s_{i,j}}{\partial u}\right| = \quad\quad E13$$

$$\sqrt{\left(\frac{\partial y_{i,j}}{\partial u}\frac{\partial z_{i,j}}{\partial v} - \frac{\partial z_{i,j}}{\partial u}\frac{\partial y_{i,j}}{\partial v}\right)^2 + \left(\frac{\partial z_{i,j}}{\partial u}\frac{\partial x_{i,j}}{\partial v} - \frac{\partial z_{i,j}}{\partial u}\frac{\partial x_{i,j}}{\partial v}\right)^2 + \left(\frac{\partial x_{i,j}}{\partial u}\frac{\partial y_{i,j}}{\partial v} - \frac{\partial y_{i,j}}{\partial u}\frac{\partial x_{i,j}}{\partial v}\right)^2}$$

When the physical x-, y-, and z-locations are used in the interpolating function, the surface are will be calculated in the square of the units of x, y, and z. At this point the calculation in the fifth block 206-10 of FIG. 20 is complete.

The second component to the mass calculation is a measurement of the thickness of the bladder muscle wall. This thickness is defined to be the normal thickness between the subserosal and submucosal surfaces of the bladder wall.

The wall thickness is calculated from the fractal dimension of the RF signal in the region of the wall thickness. The fractal dimension increases due to the multiplicity of interface reflections through the bladder muscle. The increase and decrease of fractal dimension through the bladder muscle wall can be modeled as a parabola where the fractal dimension is a function of the depth in the region of the bladder wall. The thickness of the bladder is then determined to be the region of the parabola model that is at least 97% of the maximal value of the fractal dimension. The calculations are reviewed below in equation E14.

$$fd_r = \frac{\log\left(\frac{\max(RF_{r=r-w/2,r+w/2}) - \min(RF_{r=r-w/2,r+w/2}) + w}{w}\right)}{\log\left(\frac{n}{w}\right)} \quad\quad E14$$

The wall thickness is calculated from the fractal dimension of the RF signal in the region of the wall thickness. The fractal dimension increases due to the multiplicity of interface reflections through the bladder muscle. The increase and decrease of fractal dimension through the bladder muscle wall can be modeled as a parabola where the fractal dimension is a function of the depth in the region of the bladder wall. The thickness of the bladder is then determined to be the region of the parabola model that is at least 97% of the maximal value of the fractal dimension. The calculations are reviewed below in equation 15.

The fractal dimension calculation corresponds to the fourth block 206-12 of FIG. 20. The fractal dimension is calculated for a window of length w. In the current embodiment the value of w is 5, the number of sample points along a scan line, although that value can be varied. The fractal dimension is calculated from the difference between the maximum RF signal value in the window centered at a given depth, r, and the minimum of that same window. The length of the window, w, is added to this difference, and the result is then normalized with the length of the window. The logarithm of that result is then divided by the logarithm of the ratio of the total number of samples in a scan line, n, to the length of the window. The calculation of the fractal dimension at each depth along a scan line is shown in Equation 10. This fractal dimension measure is calculated for the central n-w samples in a scan line.

After the measurements of the fractal dimension have been calculated based on the ultrasound signal, the thickness of the bladder wall may be calculated. The following calculations correspond to the seventh block 206-16 of FIG. 19.

The fractal dimension, fd, of the RF signal in the region of the bladder muscle wall is then modeled as a parabolic equation as a function of depth, r. The model of the equation for a single depth point is given in equation E15. In that equation, there are 3 parameters (a, b, and c) that define the parabola with the depth along a scan line r, and the addition of a random element ε. The subscript i indicates a specific value of r, fd, and ε.

$$fd_i = ar_i^2 + br_i + c + \epsilon_i \qquad \text{E15}$$

An equation of the form in equation E15 is obtained for each depth point in the region of the wall. The number of observations is variable and depends on the thickness of the bladder wall as observed by the ultrasound signal. Assuming a set of n observations, the subscript i would count the observations from 1 to n. The set of n equations of the form in equation 15 may be compressed into a matrix equation given in equation E16.

$$fd = X\beta + \varepsilon \qquad \text{E16}$$

$$\text{where } fd = \begin{bmatrix} fd_1 \\ fd_2 \\ \vdots \\ fd_n \end{bmatrix}, X = \begin{bmatrix} r_1^2 & r_1 & 1 \\ r_2^2 & r_2 & 1 \\ \vdots & \vdots & \vdots \\ r_n^2 & r_n & 1 \end{bmatrix}, \beta = \begin{bmatrix} a \\ b \\ c \end{bmatrix}, \text{ and } \varepsilon = \begin{bmatrix} \varepsilon_1 \\ \varepsilon_2 \\ \vdots \\ \varepsilon_n \end{bmatrix}$$

Each row of the fd, and ε, and the X matrix correspond to one of the n observations. The parabola parameters of equation E16 are collected in the vector β.

The next step is to estimate the values of the parameters of the parabola in the set of n equations of the form in equation E15 or in the matrix equation E16 based on the set of observations. A least-squares estimation of the parameters is used, and the calculation for these estimates is shown in equation E17. In E17, the t superscript indicates matrix transpose, and the −1 superscript indicates the matrix inverse. Parameters with hats (^) indicate that the value is the least-squares estimate of those parameters.

$$\hat{\beta} = (X^t X)^{-1} X^t fd \qquad \text{E17}$$

The estimates of the parabola parameters ($\hat{\beta} = [\hat{a}\ \hat{b}\ \hat{c}]^t$) can be substituted into the parabola model to calculate the estimated fractal dimension at each depth r, as shown in equation E18. The location of the maximum fractal dimension can be determined by setting the first derivative of the parabola model to equal 0 (equation E19) and solving for r. The location where the fractal dimension is maximal is given in equation E20.

$$f\hat{d}(r) = \hat{a}r^2 + \hat{b}r + \hat{c} \qquad \text{E18}$$

$$\frac{d f\hat{d}(r)}{dr} = 2\hat{a}r + \hat{b} = 0 \qquad \text{E19}$$

$$r_{fd_{max}} = -\frac{\hat{b}}{2\hat{a}} \qquad \text{E20}$$

To determine the maximal fractal dimension as defined by the parabolic model, simply substitute equation 20 into equation 18 and solve for $fd_{max}$. The resulting value is shown in equation E21.

$$f\hat{d}_{max} = \frac{-\hat{b}^2 + 4\hat{c}}{4\hat{a}}. \qquad \text{E21}$$

To determine the locations where the fractal dimension is 97% of the maximum value, multiply equation E21 by 0.97, substitute the result into equation E18 and solve for r using the quadratic formula. The locations where the fractal dimension is 97% of the maximum value, $r_{97\%}$, are given in equation E22.

$$r_{97\%} = \frac{-\hat{b} \pm \sqrt{\hat{b}^2 - 4\hat{a}\left(\hat{c} + 0.97\frac{\hat{b}^2 + 4\hat{c}}{4\hat{a}}\right)}}{2\hat{a}} \qquad \text{E22}$$

Two values for $r_{97\%}$ will be calculated from Equation 18. The difference between those two values will identify the thickness of the bladder muscle wall along the given scan line. Since these scan lines may or may not be perpendicular to the bladder muscle surface and bladder wall thickness must be measured along a line perpendicular to the bladder surface, a collection of these measurements are combined to determine the actual thickness of the bladder wall.

These measurements could be made at any surface of the bladder muscle wall. In FIG. 22, three scan lines are shown to cross the bladder muscle in two locations: the anterior wall closest to the transducer, and the posterior wall furthest from the transducer. The parabolic model described previously can be applied twice on each to determine the thickness of both the anterior and posterior wall. The maximum and minimum and mean values of these thicknesses are used in the mass calculation and historical tracking of data. In the embodiment shown, this final thickness determination marks the end of the process identified in the seventh block 206-16 of FIG. 19.

Figure 21:
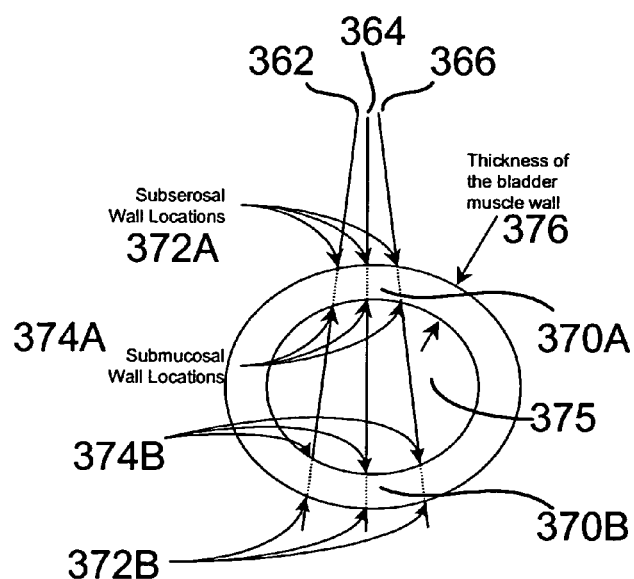
FIG. 21 is a schematic representation of three scan lines passing through the subserosal and submucosal wall locations of an organ.

FIG. 21 is a schematic representation of three scan lines passing through the subserosal and submucosal wall locations of an organ, here schematically illustrated for a bladder. Three scan lines 362, 364, and 366 penetrate the bladder. The dotted portion of the lines represents the portion of the scan lines that passes through the bladder muscle wall at an anterior or front wall location 370A and a posterior or back wall location 370B. The first 362, the second 364, and the third 366 scan lines are shown transmitting through the front subserosal wall location 372A and front submucosal wall location 374A. Similarly, the first 362, the second 364, and the third 366 scan lines are shown transmitting across the internal bladder region 375 and through the back submucosal wall location 374B and back subserosal wall location 372B. The front and back subserosal locations 372A and 372B occupy an outer bladder wall perimeter and the front and back submucosal locations 374A and 374B occupy an inner bladder wall perimeter. A bladder wall thickness value 376 is obtained for the respective differences along each scan line 362-366 between the subserosal wall locations 372A and the submucosal wall locations 374A, or the subserosal wall locations 372B and the submucosal wall locations 374B. The maximum and minimum and mean values of these thicknesses are used in the bladder wall mass calculation and historical tracking of data. In the preferred embodiment, the bladder is assumed to have a uniform wall thickness, so that a mean wall thickness value is derived from the scanned data and used for the determination of the internal wall volume 375. Only three scan lines are shown in a plane, each separated by 7.5 degrees from each other. Both the number of scan lines in the plane and the angles separating each scan line within a plane may be varied.

Once the bladder wall thickness and the inner and outer surface area have been measured, the volume of the internal bladder region 375 may be calculated by the determining the respective differences between the front and back submucosal wall locations 374A and 374B along each scanline penetrating the bladder region 375. The difference between the front and back submucosal wall locations 374A and 374B defines an inter-submucosal distance. The internal volume of the bladder region 375 is then calculated as a function of the inter-submucosal distances of the penetrating scan lines and the area of the subserosal boundary or internal bladder perimeter. The volume of internal region 375 is assumed to be the surface area times a function of the inter-submucosal distances, where the assumption is further based on a uniform wall subserosal boundary at all points around the internal bladder perimeter. In the embodiment shown, this volume calculation corresponds to the eighth block 206-20 of FIG. 19.

The methods to obtain the wall-thickness data, the mass data, and the volume of internal region 375 via downloaded digital signals can be configured by the microprocessor system for remote operation via the Internet web-based system. The Internet web-based system ("System For Remote Evaluation Of Ultrasound Information Obtained By A Program Application-Specific Data Collection Device") is described in patent application Ser. No. 09/620,766, herein incorporated by reference. The internet web-based system has multiple programs that collect, analyze, and store organ thickness and organ mass determinations. The alternate embodiment thus provides an ability to measure the rate at which internal organs undergo hypertrophy with time and permits disease tracking, disease progression, and provides educational instructions to patients.

In summary, the foregoing method supplements current algorithms in novel ways that advantageously allow different bodily fluids and/or tissues to be distinguished by volume and composition. In particular, different regions having low echogenicity may be properly distinguished. This feature advantageously permits shadowed regions of a fetus such as the arms and the legs of the fetus to be distinguished from a head region. In a diagnostic method directed to the detection of an aortic aneurysm, the foregoing embodiments may be used to differentiate shadowed regions resulting from bowel gas from other low echo regions. In a gall bladder imaging scan, the foregoing embodiments may be used to determine whether bile or other bodily fluids are within the field of view of the ultrasound-scanning device.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

We claim:

1. An ultrasonography method, comprising:
    gathering ultrasonic information pertaining to the characteristics of a tissue, a fluid, or a cavity in a biological body;
    storing the information;
    transmitting ultrasound pulses into a region-of-interest in a patient;
        receiving echoes from the region of interest, and based upon the received echoes:
            compiling an ultrasonic pattern of the region-of-interest;
            automatically comparing, with a processing device, the pattern of the region-of-interest to the characteristics of the stored information; and
            based on the automatic comparison between the pattern and the characteristics of the stored information, automatically detecting, with a processing device, a boundary between a first organ of the patient and a second organ of the patient within the region-of-interest of the patient.

2. The method of claim 1, wherein transmitting ultrasound pulses into the region of interest includes transmitting the pulses to at least one of a tissue, a fluid, and a cavity.

3. The method of claim 2, wherein transmitting the pulse further comprises transmitting the pulses to at least one of urine, blood, amniotic fluid, lung fluids, liver bile, and mixtures thereof.

4. The method of claim 1, wherein processing the pattern includes calculating at least one of a Goldberg number, a harmonic ratio, and an attenuation factor.

5. The method of claim 4, wherein processing the pattern further includes applying a window algorithm to a section of an echo pulse near a cavity-boundary interface within the region-of-interest.

6. The method of claim 5, wherein applying a window algorithm further comprises determining the harmonic frequencies associated with the section of the echo pulse near the cavity-boundary interface.

7. The method of claim 1, wherein receiving echoes further comprises receiving at least one of a single dimensional line, a two-dimensional plane, and a three-dimensional array of single dimensional lines.

8. An ultrasonography method, comprising:
    gathering ultrasonic information pertaining to the characteristics of a tissue, a fluid, or a cavity in a biological body;
    storing the information;
    transmitting ultrasound pulses into a region-of-interest in a patient;
    receiving echoes from the region of interest, and based on the echoes:
        compiling an ultrasonic pattern of the region-of-interest;
        comparing the pattern of the region-of-interest to the characteristics of the stored information; and
        based on a comparison between the pattern and the characteristics of the stored information, determining at least one of a volume, an area, and a thickness within the region-of-interest of the patient.

9. The method of claim 8, wherein transmitting ultrasound pulses to the region of interest includes transmitting the pulses into at least one of a tissue, a fluid, and a cavity.

10. The method of claim 9, wherein transmitting the pulse further comprises transmitting the pulses into at least one of urine, blood, amniotic fluid, lung fluids, liver bile, and mixtures thereof.

11. The method of claim 8, wherein processing the pattern includes calculating at least one of a Goldberg number, a harmonic ratio, and an attenuation factor.

12. The method of claim 8, wherein processing the pattern further includes applying a window algorithm to a section of an echo pulse near a cavity-boundary interface within the region-of-interest.

13. The method of claim 12, wherein applying a window algorithm further comprises determining one or more harmonic frequencies associated with the section of the echo pulse near the cavity-boundary interface.

14. The method of claim 8, wherein receiving echoes further comprises receiving at least one of a single dimensional line, a two-dimensional plane, and a three-dimensional array of single dimensional lines.

15. The method of claim 8, wherein determining the volume within the region of interest includes determining a volume of at least one cavity.

16. The method of claim 15, wherein determining a volume of at least one cavity further comprises determining a volume of at least one of a bladder and a uterus.

17. The method of claim 16, wherein determining a volume of at least one of a bladder and a uterus further comprises determining a volume of the bladder after fluid has been voided from the bladder.

18. An ultrasonography method, comprising:
gathering information representing the characteristics of a tissue, a fluid, or cavity in a body;
storing the gathered information;
transmitting ultrasound pulses into a region-of-interest in a patient;
receiving echoes from the region of interest, and based upon the received echoes:
compiling an ultrasound harmonic of the region-of-interest;
automatically comparing, with a processing device, the harmonic of the region-of-interest to the characteristics of the stored information; and
automatically detecting, with a processing device, a boundary between a first organ of the patient and a second organ of the patient within the region-of-interest of the patient based upon the automatic comparison of the harmonic with the stored information.

19. The method of claim 18, wherein the harmonic comprises a second harmonic.

20. An ultrasonography method, comprising:
gathering information representing the characteristics of a tissue, a fluid, or cavity in a body;
storing the gathered information;
transmitting ultrasound pulses into a region-of-interest in a patient;
receiving echoes from the region of interest, and based upon the received echoes:
compiling an ultrasound harmonic of the region-of-interest;
comparing the harmonic of the region-of-interest to the characteristics of the stored information; and
determining a volume within the region-of-interest of the patient based upon the comparison of the harmonic with the stored information.

21. The method of claim 20, wherein the harmonic further includes a second harmonic.

22. An ultrasonography method, comprising:
gathering ultrasonic information pertaining to the characteristics of a tissue, a fluid, or a cavity in a biological body;
storing the information;
transmitting ultrasound pulses into a region-of-interest in a patient;
receiving echoes from the region of interest, and based upon the received echoes:
compiling an ultrasonic pattern of the region-of-interest;
automatically comparing, with a processing device, the pattern of the region-of-interest to the characteristics of the stored information; and
based on a comparison between the pattern and the characteristics of the stored information, automatically distinguishing, with a processing device, a first fluid composition of the patient from a second fluid composition of the patient within the region-of-interest of the patient.

23. An ultrasonography method, comprising:
gathering ultrasonic information pertaining to the characteristics of a tissue, a fluid, or a cavity in a biological body;
storing the information;
transmitting ultrasound pulses into a region-of-interest in a patient;
receiving echoes from the region of interest, and based upon the received echoes:
compiling an ultrasonic pattern of the region-of-interest;
automatically comparing, with a processing device, the pattern of the region-of-interest to the characteristics of the stored information; and
based on a comparison between the pattern and the characteristics of the stored information, automatically distinguishing, with a processing device, a first fluid composition of the patient from a first organ of the patient within the region-of-interest of the patient.

* * * * *